United States Patent [19]

Nakamura et al.

[11] Patent Number: 4,950,764
[45] Date of Patent: Aug. 21, 1990

[54] 2-ARYL-4-ISOXAZOLIN-3-ONE DERIVATIVES

[75] Inventors: Koki Nakamura; Shigeru Makamura, both of Kanagawa, Japan

[73] Assignees: Fuji Photo Film Co., Ltd., Kanagawa, Japan;

[21] Appl. No.: 189,072

[22] Filed: May 2, 1988

[30] Foreign Application Priority Data

Apr. 30, 1987 [JP] Japan ................. 62-106896

[51] Int. Cl.$^5$ ............................................. G03C 1/06
[52] U.S. Cl. ................................... 248/243; 548/257; 548/129; 548/182; 548/325; 548/251
[58] Field of Search ........................................ 548/243

[56] References Cited

FOREIGN PATENT DOCUMENTS 0220746 6/1987 European Pat. Off. .
0306833 3/1989 European Pat. Off. .
287857 11/1988 Japan .

Primary Examiner—Mukund J. Shah
Assistant Examiner—C. L. Cseh
Attorney, Agent, or Firm—Sughrue, Mion, Zinn, Macpeak & Seas

[57] ABSTRACT

2-Aryl-4-isoxazolin-3-one derivatives having the following general formula (I):

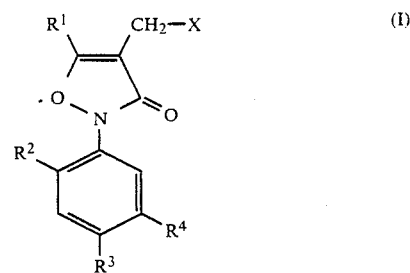

wherein $R^1$ represents an alkyl group or an aryl group, $R^2$, $R^3$, and $R^4$ each represents a hydrogen atom, a trifluoromethyl group, a carbamoyl group, a sulfamoyl group, an alkoxycarbonyl group, an aryloxycarbonyl group, a sulfonyl group, a halogen atom, a cyano group, a nitro group, an alkoxy group, an aryloxy group, an acyl group, a carboxy group, or a sulfo group, with at least one of $R^2$, $R^3$, and $R^4$ being selected from among a nitro group, a cyano group, a sulfamoyl group, a carbamoyl group, and a sulfonyl group, and X represents a monovalent group of one of a mercaptoazole, a mercaptoazaindene, a tetrazaindene, a mercaptopyrimidine a benzotriazole, an indazole, and a benzimiazole, are disclosed.

19 Claims, No Drawings

2-ARYL-4-ISOXAZOLIN-3-ONE DERIVATIVES

FIELD OF THE INVENTION

This invention relates to 2-aryl-4-isoxazolin-3-one derivatives.

BACKGROUND OF THE INVENTION

Examples and processes for the preparation of 2-arylisoxazolin-3-one derivatives are described in *Heterocycles*, 20(6), pp.1123–1126 (1983), *Chemical and pharmaceutical Bulletin*, 30(9), pp.3097–3105, *Heterocycles*, 19(3), pp.515–520, *Heterocycles*, 19(3), pp.521–524, *Journal of the Heterocyclic Chemistry*, 17(4), pp.727–731, *Chemical and Pharmaceutical Bulletin*, 19(7), pp.1389–1394, Japanese Patent Application (OPI) No. 104,274/80 (the term "OPI" as used herein means an "unexamined published application"), etc. However, derivatives where the substituent in the 2-position is an aryl group having a group which is more electron attractive than a chlorine atom are not known. Also, derivatives where a methyl group mono-substituted by a nitrogen or sulfur atom is bound to the 4-position are not known.

SUMMARY OF THE INVENTION

An object of the present invention is to provide novel 2-aryl-4-isoxazolin-3-one derivatives having a methyl group mono-substituted by a nitrogen or a sulfur atom of a mercaptoazole, a mercaptoazaindene, a mercaptopyrimidine, a benzotriazole, an indazole or a benzimidazole group at the 4-position and a group which is more electron attracting than a chlorine atom (i.e., a group having a Hammett's substituent constant $\delta_p$ of higher than 0.227) in an aryl moiety at the 2-position.

The compounds of the present invention are represented by the following formula (I):

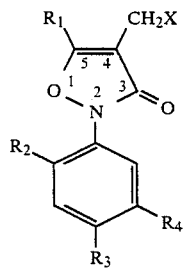

In the above general formula, $R^1$ represents an alkyl group (including those having a substituent or substituents; for example, a methyl group, an ethyl group, an isopropyl group, a cyclohexyl group, a t-butyl group, a chloromethyl group, an N-methylacetylaminomethyl group, an octylthiomethyl group, an adamantyl group, an undecyl group, a heptadecyl group, etc.) or an aryl group (including those having a substituent or substituents; for example, a phenyl group, a 2-methylphenyl group, a 4-methylphenyl group, a 4-methoxyphenyl group, a 3-methoxy-4-acetamidophenyl group, a 4-dodecyloxyphenyl group, a 4-hexadecyloxyphenyl group, a 3-sulfo-4-methoxyphenyl group, etc.). As the alkyl group, those which contain 1 to 6 carbon atoms are preferred and, as the aryl group, those which contain 6 to 24 carbon atoms are preferred. Particularly preferred examples of $R^1$ are a methyl group, a t-butyl group, a phenyl group, an alkoxy group-substituted phenyl group and a sulfo group-substituted phenyl group.

$R^2$, $R^3$, and $R^4$ each represents a group selected from among an alkoxy group (including those having a substituent or substituents; for example, a methoxy group, a 2-methoxyethoxy group, an ethoxy group, a n-hexyloxy group, a n-hexadecyloxy group, a methoxypropyl group, etc.), an aryloxy group (including those having a substituent or substituents; for example, a phenoxy group, a 4-n-hexadecylcarbamoylphenoxy group, etc.), an acyl group (including those having a substituent or substituents; for example, an acetyl group, a n-dodecanoyl group, a benzoyl group, a 2-ethoxycarbonylbenzoyl group, a 2,2-dimethylpropanoyl group, etc.), an alkoxy or aryloxycarbonyl group (including those having a substituent or substituents; for example, a methoxycarbonyl group, an ethoxycarbonyl group, a n-octyloxycarbonyl group, a n-hexadecyloxycarbonyl group, a phenoxycarbonyl group, etc.), a sulfonyl group (including those having a substituent or substituents; for example, a methylsulfonyl group, a chloromethylsulfonyl group, an ethylsulfonyl group, a n-dodecylsulfonyl group, a n-tetradecylsulfonyl group, a phenylsulfonyl group, a 4-methylphenylsulfonyl group, a t-dodecylsulfonyl group, etc.), a carbamoyl group (including those having a substituent or substituents; for example, a carbamoyl group, a dimethylcarbamoyl group, a diethylcarbamoyl group, a n-butylcarbamoyl group, a 3-(2,4-di-t-pentylphenoxy)propylcarbamoyl group, an N-methyl-N-n-octylcarbamoyl group, a (3-hexadecylsulfamoyl) phenylcarbamoyl group, an N-methyl-N-n-octadecylcarbamoyl group, a n-hexadecylcarbamoyl group, a 3-n-dodecyloxypropylcarbamoyl group, etc.), a sulfamoyl group (including those having a substituent or substituents; for example, a methylsulfamoyl group, a dimethylsulfamoyl group, a diethylsulfamoyl group, a dibutylsulfamoyl group, an N-methyl-N-n-hexylsulfamoyl group, an N-methyl-N-n-octylsulfamoyl group, an N-methyl-N-n-hexadecylsulfamoyl group, an N-methyl-N-n-octadecylsulfamoyl group, a n-dodecylsulfamoyl group, an N-phenyl-N-n-hexadecylsulfamoyl group, an N-methyl-N-3-methoxypropylsulfamoyl group, a bis(2-methoxyethyl)sulfamoyl group,

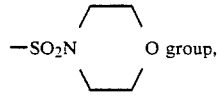

etc.), a nitro group, a cyano group, a halogen atom, a carboxyl group, a trifluoromethyl group, and a sulfo group, with at least one of $R^2$ and $R^3$ being selected from among a nitro group, a cyano group, a sulfonyl group or a trifluromethyl group. At least one of $R^2$ and $R^3$ preferably represents a nitro or a sulfonyl group. Particularly preferably, at least one of $R^2$ and $R^3$ represents a nitro group.

When at least one of $R^2$ and $R^3$ represents a nitro group, the other group and/or $R^4$ preferably represents a sulfonyl group, a sulfamoyl group, an alkoxycarbonyl group, a carbamoyl group, an acyl group, a trifluoromethyl group, a cyano group, a carboxy group or a sulfo group.

In particular, those compounds where $R^2$ represents a nitro group, $R^3$ represents a sulfamoyl group, a carbamoyl group, an alkoxycarbonyl group, a trifluoromethyl group, a carboxy group or a sulfo group, and $R^4$ represents a hydrogen atom are preferred.

As the alkoxy group, acyl group, alkoxy or aryloxycarbonyl group and sulfonyl group, those which contain not more than 20 carbon atoms are preferred. As the carbamoyl group and sulfamoyl group, those which contain not more than 36 carbon atoms are preferred.

X represents one of a mercaptoazole, a mercaptoazaindene, a mercaptopyrimidine, a benzotriazole, an indazole, and a benzimidazole (including those having a substituent or substituents) which is bound to the methylene carbon at the 4-position of the 4-isoxazoline ring through the sulfur or nitrogen atom.

Of these, preferred compounds are illustrated below in terms of the name of group X:
a 1-phenyl-5-tetrazolylthio group;
a 1-(4-carboxyphenyl)-5-tetrazolylthio group;
a 1-(3-hydroxyphenyl)-5-tetrazolylthio group;
a 1-(4-sulfophenyl)-5-tetrazolylthio group;
a 1-(3-sulfophenyl)-5-tetrazolylthio group;
a 1-(4-sulfamoylphenyl)-5-tetrazolylthio group;
a 1-(3-hexanoylaminophenyl)-5-tetrazolylthio group;
a 1-(3-nonanoylaminophenyl)-5-tetrazolylthio group;
a 1-(3-aminophenyl)-5-tetrazolylthio group;
a 1-(1-naphthyl)-5-tetrazolylthio group;
a 1-(3-(3-methylureido)phenyl)-5-tetrazolylthio group;
a 1-(4-nitrophenyl)-5-tetrazolylthio group;
a 1-(3-phenoxycarbonylphenyl)-5-tetrazolylthio group;
a 1-(4-phenoxycarbonylphenyl)-5-tetrazolylthio group;
a 1-(3-maleinimidophenyl)-5-tetrazolylthio group;
a 1-ethyl-5-tetrazolylthio group;
a 1-(2-carboxyethyl)-5-tetrazolylthio group;
a 1-(4-benzoyloxyphenyl)-5-tetrazolylthio group;
a 1-(3-vinylcarbonylphenyl)-5-tetrazolylthio group;
a 2-methylthio-5-(1,3,4-thiadiazolyl)thio group;
a 2-pentylthio-5-(1,3,4-thiadiazolyl)thio group;
a 2-(2-carboxyethylthio)-5-(1,3,4-thiadiazolyl)thio group;
a 2-(2-dimethylaminoethylthio)-5-(1,3,4-thiadiazolyl)thio group;
a 2-phenoxycarbonylmethylthio-5-(1,3,4-thiadiazolyl)thio group;
a 2-(3-(thiophen-2-ylcarbonyl)propyl)thio-5-(1,3,4-thiadiazolyl)thio group;
a 2-benzothiazolylthio group;
a 5-(2-methanesulfonylethoxycarbonyl)-2-benzothiazolylthio group;
a 2-benzimidazolylthio group;
a 1-(4-n-hexylcarbamoylphenyl)-2-imidazolylthio group;
a 1-phenyl-2-imidazolylthio group;
a 5-(2-ethylhexanoylamino)-2-benzimidazolylthio group;
a 5-hexanoylamino-2-benzimidazolylthio group;
a 5-phenoxycarbonyl-2-benzimidazolylthio group;
a 1-(4-(2-chloroethoxycarbonyl)phenyl)-2-imidazolylthio group;
a 2-benzoxazolylthio group;
a 2-(6-nitro-1,3-benzoxazolyl)thio group;
a 6-phenoxycarbonyl-2-benzoxazolylthio group;
a 3-methyl-4-phenyl-5-(1,2,4-triazolyl)thio group;
a 3-acetylamino-4-methyl-5-(1,2,4-triazolyl)thio group;
a 2-phenyl-5-(1,3,4-oxadiazoyl)thio group;

a 6-methyl-4-(1,3,3a,7-tetrazaindenyl)thio group;
a 6-methyl-2-benzyl-4-(1,3,3a,7-tetrazaindenyl)thio group;
a 6-phenyl-4-(1,3,3a,7-tetrazaindenyl)thio group;
a 4,6-dimethyl-2-(1,3,3a,7-tetrazaindenyl)thio group;
a 2-pyrimidinylthio group;
a 4-methyl-6-hydroxy-2-pyrimidinylthio group; and
a 4-propyl-2-pyrimidinylthio group.

These groups are bound to the methylene carbon at the 4-position of the 4-isoxazoline ring through the sulfur atom.

Further there are illustrated:
a benzotriazolyl group;
a 5-nitrobenzotriazolyl group;
a 5-methylbenzotriazolyl group;
a 5,6-dichlorobenzotriazolyl group;
a 5-bromobenzotriazolyl group;
a 5-methoxybenzotriazolyl group;
a 5-acetylaminobenzotriazolyl group;
a 5,6-dimethylbenzotriazolyl group;
a 5-n-butylbenzotriazolyl group;
a 5-nitro-6-chlorobenzotriazolyl group;
a 4,5,6,7-tetrachlorobenzotriazolyl group;
a 5-phenoxycarbonylbenzotriazolyl group;
a 5-(2,3-dichloropropyloxycarbonyl)benzotriazolyl group;
a 5-benzyloxycarbonylbenzotriazolyl group;
a 5-(butylcarbamoylmethoxycarbonyl)benzotriazolyl group;
a 5-(butoxycarbonylmethoxycarbonyl)benzotriazolyl group;
a 5-succinimidomethylbenzotriazolyl group;
an indazolyl group;
a 5-nitroindazolyl group;
a 3-nitroindazolyl group;
a 3-chloro-5-nitroindazolyl group;
a 3-cyanoindazolyl group;
a 3-n-butylcarbamoylindazolyl group;
a 5-nitro-3-methanesulfonylindazolyl group;
a 5-nitro-3-phenoxycarbonylindazolyl group;
a 5-nitrobenzimidazolyl group;
a 4-nitrobenzimidazolyl group;
a 5,6-dichlorobenzimidazolyl group;
a 5-cyano-6-chlorobenzimidazolyl group; and
a 5-trifluoromethyl-6-chflorobenzimidazolyl group.

These groups are bound to the methylene carbon in the 4-position of the 4-isoxazoline ring through the nitrogen atom.

Of the above-illustrated X groups, more preferred examples are a 1-phenyl-5-tetrazolylthio group, a 2-methyl-thio-5-(1,3,4-thiadiazolyl)thio group, a 2-benzothiazolylthio group, a 2-benzimidazolylthio group, a 5-nitrobenzotriazolyl group, a 5-nitrobenzindazolyl group, and a 6-methylbenzotriazolyl group.

Of these X groups, a 1-phenyl-5-tetrazolylthio group, a 2-methyl-5-(1,3,4-thiadiazolyl)thio group, a 2-benzothiazolylthio group, and a 2-benzimidazolylthio group which are bound to the methylene carbon at the 4-position of the 4-isoxazoline ring through sulfur atom are preferred, with a 1-phenyl-5-tetrazolylthio group being most preferred.

Specific examples of the compounds of the present invention are illustrated below which, however, do not limit the present invention in any way.

| Compound No. | Structure | mp |
|---|---|---|
| 1 | (structure shown) | 120° C. |
| 2 | (structure shown) | 94~96° C. |
| 3 | (structure shown) | 64~66° C. |
| 4 | (structure shown) | Oil |

-continued

| Compound No. | Structure | mp |
|---|---|---|
| 5 | 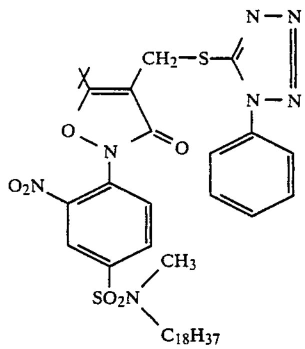 | 91~92° C. |
| 6 | 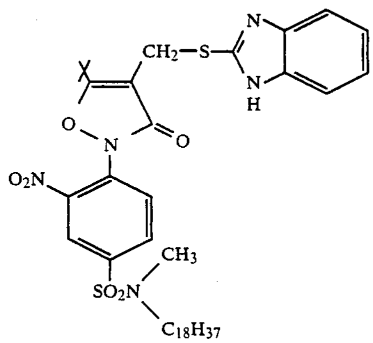 | 102~104° C. |
| 7 | 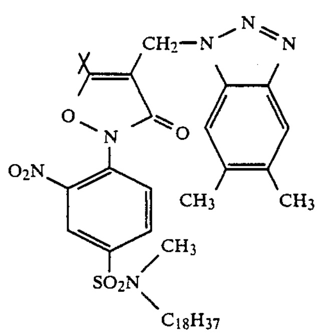 | 97~98° C. |
| 8 | 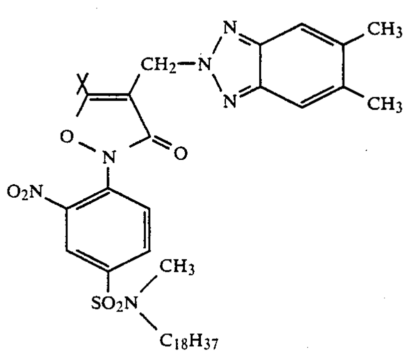 | 84~85° C. |

-continued

| Compound No. | Structure | mp |
|---|---|---|
| 9 | 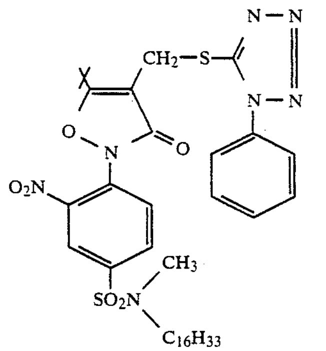 | 73~75° C. |
| 10 | 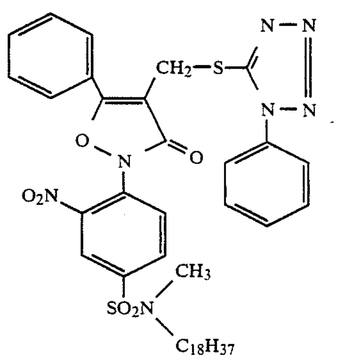 | 117~118° C. |
| 11 | 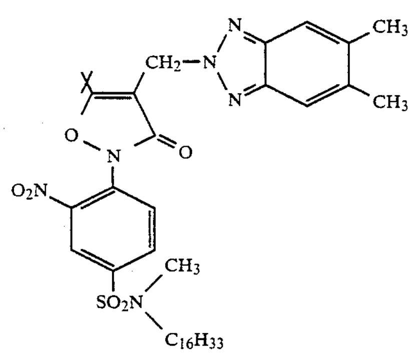 | 80~81° C. |
| 12 | 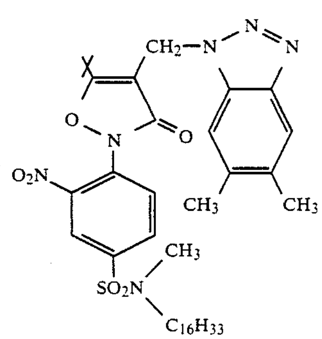 | 94~96° C. |

-continued

| Compound No. | Structure | mp |
|---|---|---|
| 13 | 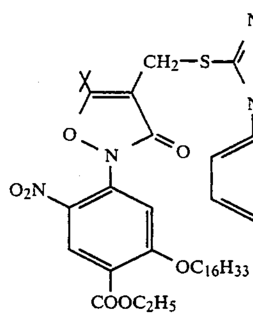 | Oil |
| 14 | 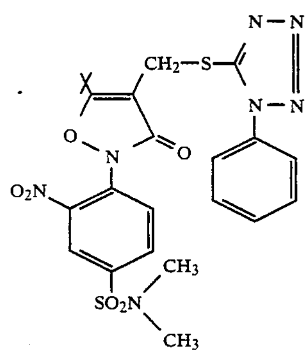 | 172~173° C. |
| 15 | 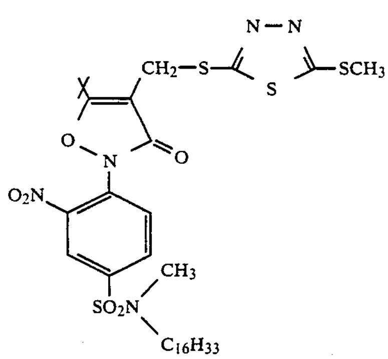 | 65~66° C. |
| 16 | 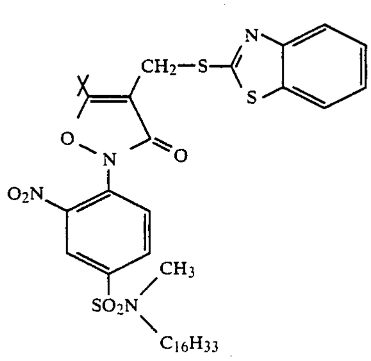 | 81~82° C. |

-continued

| Compound No. | Structure | mp |
|---|---|---|
| 17 | 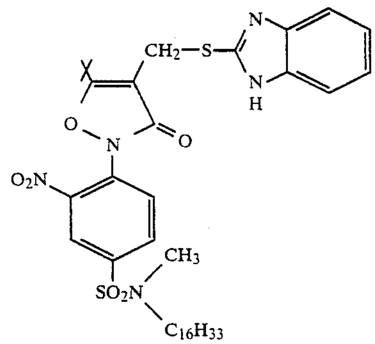 | 93~95° C. |
| 18 | 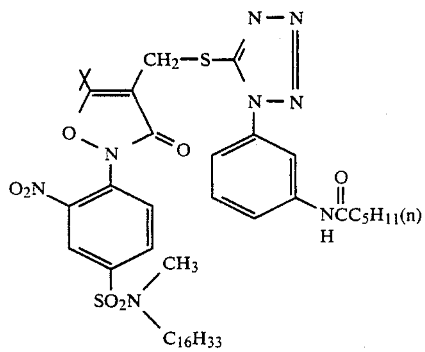 | 107~108° C. |
| 19 | 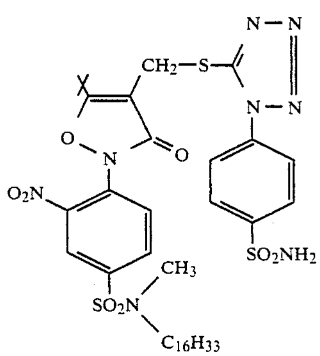 | 91~93° C. |
| | a mixture of | |
| 20 | 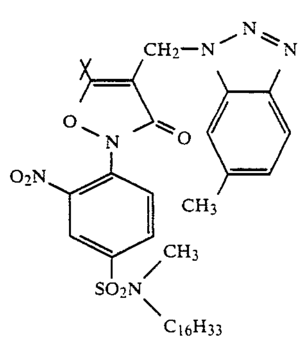 | 63~70° C. |
| | and | |

|Compound No.|Structure|mp|
|---|---|---|
| | 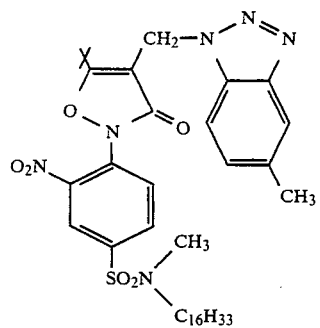 | |
| 21 | 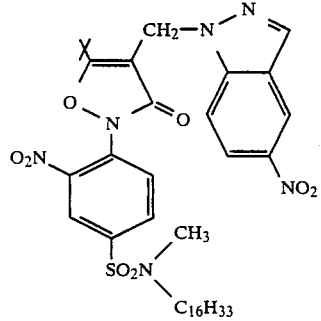 | 96~98° C. |
| 22 | 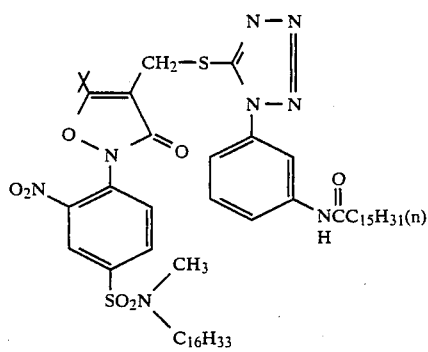 | 105~106° C. |
| 23 | 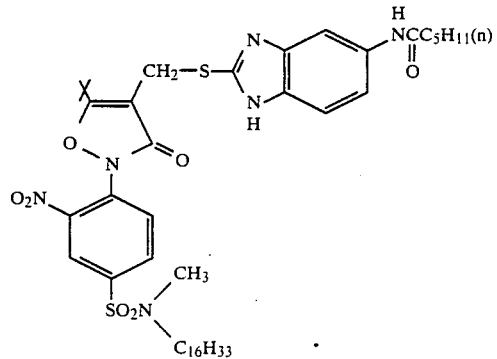 | 83~85° C. |

| Compound No. | Structure | mp |
|---|---|---|
| 24 | 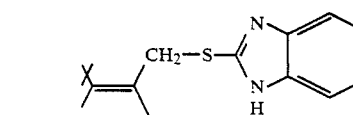 | 225° C.~ (decomposition)* |
*This compound begins to melt at 225° C. and then gradually blackens and decomposes, but its decomposition temperature cannot be defined.
| | | |
|---|---|---|
| 25 | 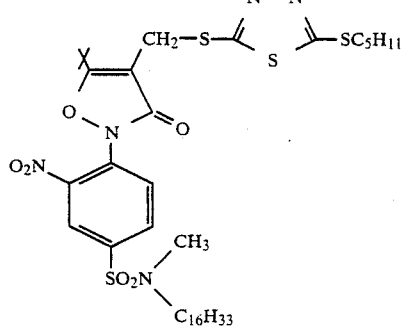 | 60~61° C. |
| 26 | 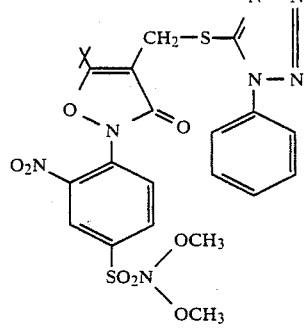 | 121~123° C. |
| 27 | 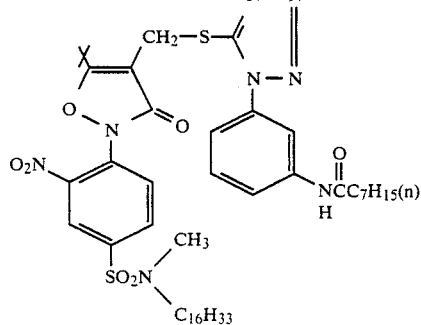 | 102~104° C. |

-continued

| Compound No. | Structure | mp |
|---|---|---|
| 28 | 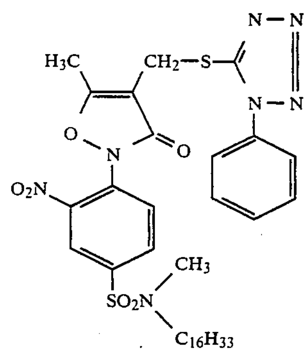 | 81~82° C. |
| 29 | 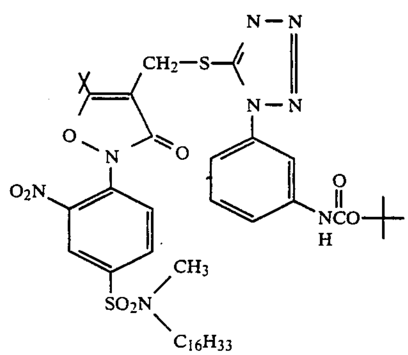 | 77~78° C. |
| 30 | 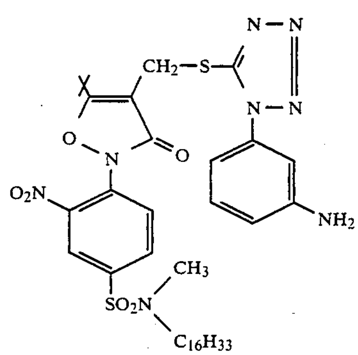 | 79~81° C. |
| 31 | 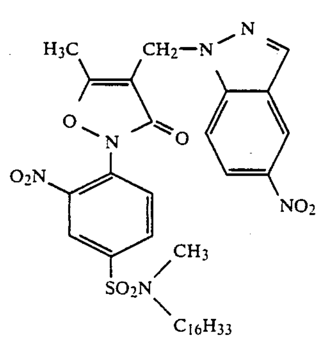 | 63~70° C. |

-continued

| Compound No. | Structure | mp |
|---|---|---|
| 32 | (structure) | 60~62° C. |
| 33 | (structure) | 122~123° C. |
| 34 | (structure) | Oil |
| 35 | (structure) | 74~76° C. |

| Compound No. | Structure | mp |
|---|---|---|
| 36 | 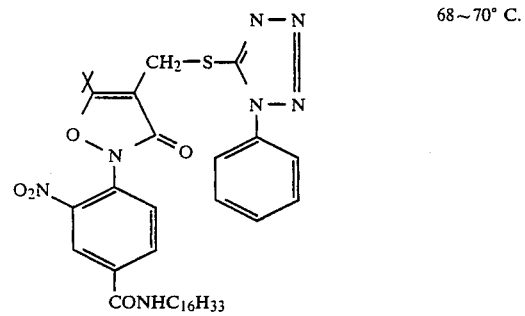 | 68~70° C. |
| 37 | 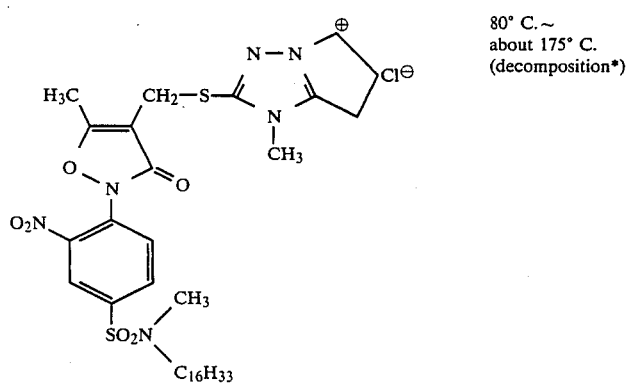 | 80° C.~ about 175° C. (decomposition*) |
*This compound begins to melt at 80° C. and decomposes at about 175° C.
| | | |
|---|---|---|
| 38 | 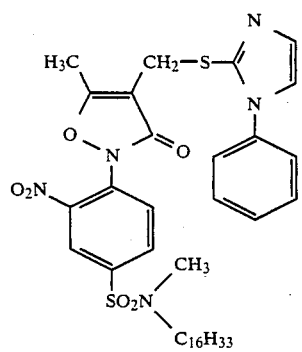 | 46~47° C. |
| 39 | 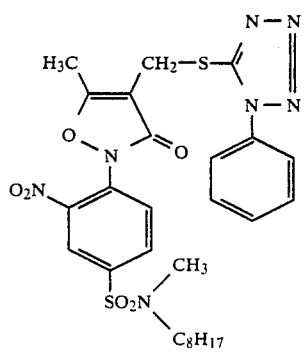 | 77~79° C. |

| Compound No. | Structure | mp |
|---|---|---|
| 40 | (structure) | 105~106° C. |
| 41 | (structure) | 73~76° C. |
| 42 | (structure) | 88~90° C. |
| 43 | (structure) | 179~181° C. |

-continued
| Compound No. | Structure | mp |
|---|---|---|
| 44 | 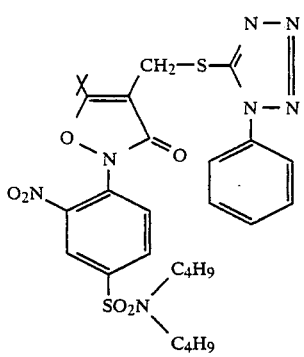 | 146~147° C. |
| 45 | 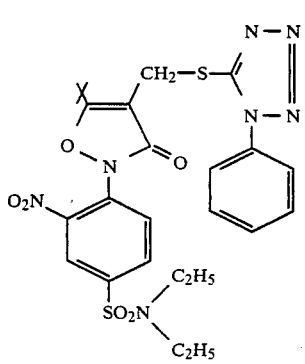 | 148~150° C. |
| 46 | 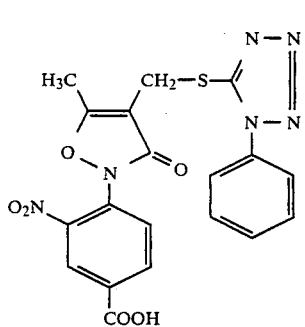 | 192~194° C. |
| 47 | 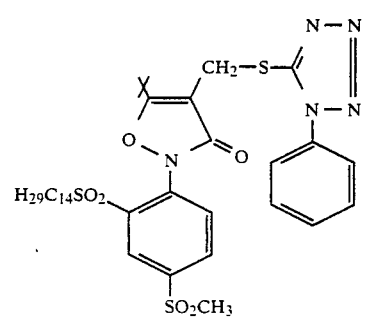 | 127~129° C. |

| Compound No. | Structure | mp |
|---|---|---|
| 48 | 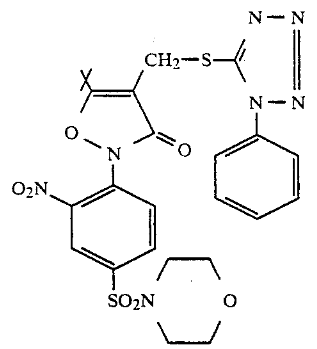 | 186~188° C. |
| 49 | 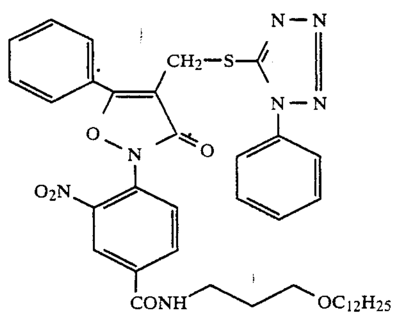 | 40~42° C. |
| 50 | 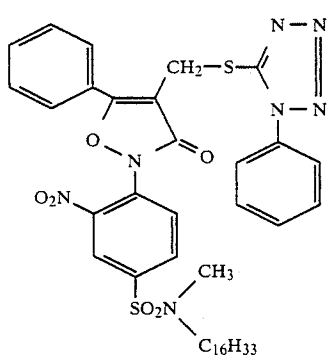 | 121~123° C. |
| 51 | 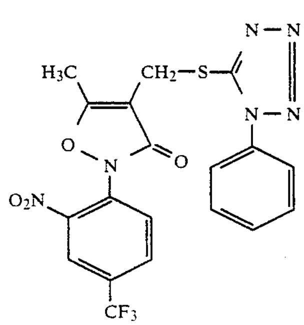 | 88~90° C. |

| Compound No. | Structure | mp |
|---|---|---|
| 52 | 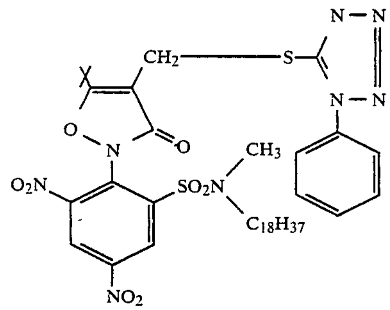 | 53~55° C. |
| 53 | 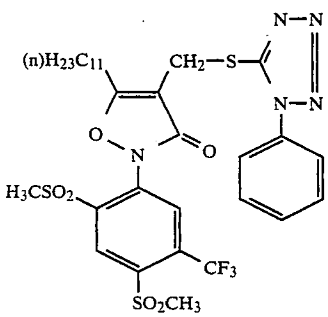 | 113~116° C. |
| 54 | 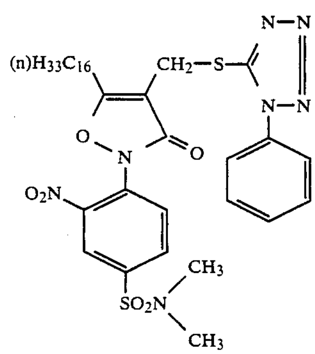 | 145~146° C. |
| 55 | 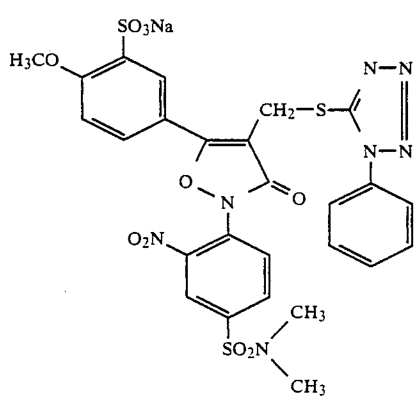 | >260° C. |

-continued

| Compound No. | Structure | mp |
|---|---|---|
| 56 | (structure) | 84~85° C. |
| 57 | (structure) | 80~83° C. |
| 58 | (structure) | 141~142° C. |
| 59 | (structure) | 159~161° C. |

-continued

| Compound No. | Structure | mp |
|---|---|---|
| 60 | (structure) | 203~205° C. |
| 61 | (structure) | 119~122° C. |
| 62 | (structure) | Oil |
| 63 | (structure) | >260° C. |
| 64 | (structure) | >260° C. |

4,950,764

| Compound No. | Structure | mp |
|---|---|---|
| 65 | 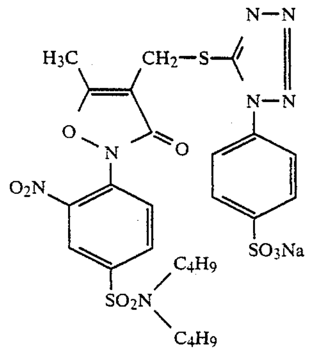 | >260° C. |
| 66 | 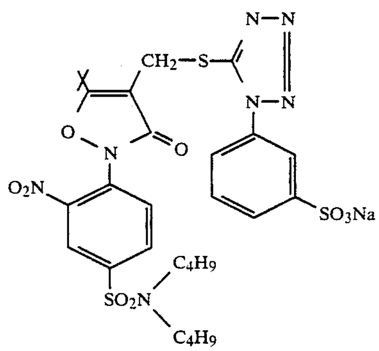 | >260° C. |
| 68 | 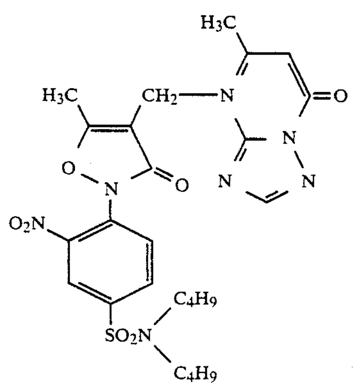 | 48~51° C. |
| 69 | 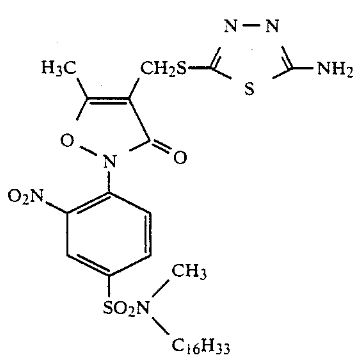 | 72~74° C. |

In the above formulae, ╂ represents CH₃—C(CH₃)₂—CH₃ (i.e., $CH_3-C(CH_3)_2-$, with CH₃ above and CH₃ below), and ⌒⌒ represents —CH₂—CH₂—CH₂—.

The 2-Aryl-4-isoxazolin-3-one derivatives which are synthesis intermediates for the compounds of the pres- (A) A process of N-acrylating a nitrogen-substituted hydroxylamine with a propiolic acid derivative (an ester 7 or an acid halide) and ring-closing the acrylated product under basic conditions to obtain a 4-isoxazolin-3-one derivative (examples are given in *Chemical Abstracts*, vol.76, No. 23, 140775a, ibid., vol.75, No.17, 110227k, etc.) and a process of N-acrylating a nitrogen-substituted hydroxylamine with diketene or a β-keto-acid derivative and conducting dehydration ring closure to obtain a 4-isoxazolin-3-one derivative (examples are given in *Heterocycles*, vol.20, No.6, pp.1123–1126, ibid., vol.19, No.3, pp.521–524, etc.).

(B) A process of conducting a substitution reaction between an aromatic compound having an electron attracting group at the 2-position or its conjugation position and which is active for aromatic nucleophilic substitution such as a halobenzene and a 3-hydroxyisoxazole in an aprotic polar solvent such as dimethylsulfoxide or dimethylformamide under basic condition to obtain a 4-isoxazolin-3-one derivative.

As a process for synthesizing a 2-aryl-4-halomethyl-4-isoxazoline-3-one derivative, which is a starting material for synthesizing the compounds of the present invention, from the 2-aryl-4-isoxazoline-3-one derivative synthesized according to the above-described reactions, there is illustrated the following process That is, the starting material can be obtained by heating (about 50° C. to about 120° C.) for several minutes to several hours a mixture of the 2-aryl-4-isoxazolin-3-one derivative, an excess amount (usually about 3 to about 20 equivalents) of paraformaldehyde, and about 1 to about 2 equivalents of anhydrous zinc chloride in a solvent of the halogen type (e.g., methylene chloride, chloroform, or 1,2-dichloroethane) or acetic acid while blowing hydrogen chloride gas thereinto in an amount of saturation. The amount of the solvent is usually about 2 to about 20 times by weight that of the 2-aryl-4-isoxazolin-3-one derivative.

As a process for synthesizing the compounds of the present invention from the thus synthesized 2-aryl-4-halomethyl-4-isoxazoline-3-one, there is now illustrated a general synthesis process.

That is, the 2-aryl-4-halomethyl-4-isoxazoline-3-one derivative is mixed with an about 1 to about 2 equivalents of a mercaptoazole, a mercaptoazaindene, a mercaptopyrimidine, a benzotriazole, an indazole, or a benzimidazole compound using as a solvent acetone, acetonitrile, an alcohol, ethyl acetate or the like, and an about 1 or more equivalents of acid-neutralizing agent (alkali agent) (e.g., an inorganic base such as potassium carbonate, sodium hydrogen carbonate etc., an organic base such as pyridine, triethylamine, etc.) and if, necessary, a catalytic amount (about 0.1 to about 10 wt % based on the total weights of the reaction component) of sodium iodide are added to the mixture, followed by stirring for several minutes to several hours, usually at room temperature. In this process, the amount of the solvent is usually about 2 to about 20 times by weight that of the 2-aryl-4-halomethyl-4-isoxazoline-3-one derivative. The amount of the acid-neutralizing agent does not exceed 10 times by weight that of the 2-aryl-4-halomethyl-4-isoxazoline-3-one derivative.

The compounds of the present invention fall into the category of compounds called positive-working compounds in the field of silver halide photographic light-sensitive materials and release a photographically active compound (a heterocyclic compound referred to for defining X in formula (1)) upon an oxidation-reduction reaction and, as a result, they mainly exert an antifogging effect, a development-preventing effect, and other effects on undeveloped area or whole area. In addition, they are novel compounds which are extremely stable in a photographic system which permits one to freely control their activity upon photographic processing. Specific effectiveness of them are as described in U.S. patent application Ser. No 925,350 (filed on Oct. 30, 1986), Japanese Patent Application Nos. 259,326/86, 287,455/86, 34,955/87, 88,625/86, etc.

Further, they possess pharmacological effects as herbicides, bactericides, analgesics, antiinflammatory agents, etc. and are therefore also of importance as physiologically active substances.

The present invention is now illustrated in greater detail by reference to the following examples which, however, are not to be construed as limiting the present invention in any way.

EXAMPLE 1

Synthesis of Compound 9:

Synthesis Example 1-1:

Synthesis of 3-hydroxyisoxazoles

The above-described compounds can be easily synthesized by reference to processes described in the following literature and patents "Annual Report of Sankyo Institute", vol.22, p.215 (1970); Japanese Patent Publication No. 9,675/77; "Bulletin de la societe chmique de France", p.1978; Japanese Patent Application (OPI) Nos. 206,668/82 and 206,667/82, "Tetrahedron", vol.20, p.2835 (1964); Japanese Patent Application Nos. 194,867/83 and 70,878/82; Japanese Patent Publication No. 48,953/74; Japanese Patent Application (OPI) No. 190,977/84; "Journal of Organic Chemistry", vol.48, p.4307 (1983); "Chemical and Pharmaceutical Bulletin", vol. 14, p.277; "Heterocycles" vol.12, No.10, p.1297; "Canadian Journal of Chemistry", vol.62, p.1940; and WO No. 8401774.

Specific procedures are now given.

(Example 1) Synthesis of 5-t-butyl-3-hydroxyisoxazole 583.7 g of hydroxylamine hydrochloride was dissolved in 2 liters of a 4N sodium hydroxide aqueous solution, 2 liters of ethanol was added thereto under ice cooling, and a solution of a mixture of 4N sodium hydroxide and ethanol (1:1 vol.) was added thereto to adjust the pH of the solution to 10.0. To this solution were dropwise added 1380 g of ethyl pivaloylacetate and a solution of a mixture of 4N sodium hydroxide and ethanol (1:1 vol.) while controlling the pH of the reaction solution to 10.0±0.2 and the temperature to −5° C.

After completion of the dropwise addition, the reaction solution was stirred at room temperature for 2 hours, then poured into 6 kg of a 0° C. concentrated hydrochloric acid aqueous solution followed by letting the resulting solution stand for 12 hours at room temperature. The crystals which precipitated were collected by filtration, washed well with water, and dried.

Yield: 770 g (68.2 %); mp: 99°–101 ° C.

(Example 2) Synthesis of 5-phenyl-3-hydroxyisoxazole

The above -identified compound was synthesized according to the process described in "Chemical and Pharmaceutical Bulletin", vol.14, No.11, pp.1277–1286.
mp: 150°–151 ° C.

(Example 3) Synthesis of 5-undecyl-3-hydroxyisoxazole

The above-identified compound was synthesized according to the process of (Example 1) using hydroxylamine hydrochloride and dodecanoylacetic acid ethylester as raw materials.

Yield: 59.2%, mp: 55°–56 ° C.

(Example 4) Synthesis of 5-methyl-3-hydroxyisoxazole

The above-identified compound was synthesized according to the process described in Example 1 of WO No. 8401774 using hydroxylamine hydrochloride and methyl acetoacetate.

mp: 85°–86 ° C.

(Example 5) Synthesis of 5-(4-methoxyphenyl)-3-hydroxyisoxazole

The above-identified compound was synthesized according to the process of (Example 2) using hydroxylamine hydrochloride and 4-methoxybenzoylacetic acid ethylester.

mp: 191°–193 ° C. (decomposition)

Other 3-hydroxyisoxazoles may be synthesized in the same manner.

Synthesis Example 1-2: Synthesis of N-hexadecyl-3-nitro-4-chlorobenzenesulfonamide 800 g of 3-nitro-4-chlorobenzenesulfonyl chloride was mixed with 1,000 ml of dichloromethane, and a solution of 600 g of hexadecylamine and 251 ml of triethylamine in dichloromethane was dropwise added thereto. After completion of the reaction, the reaction solvent was removed under reduced pressure, 3,000 ml of methanol was added to the residue, and the mixture was heated to dissolve the system. Gradual cooling of the solution gave crystals. The crystals were collected by filtration and dried.

Yield: 1020 g (88 %); mp: 91°–93 ° C.

Synthesis Example 1-3: Synthesis of N-methyl-N-hexadecyl-3-nitro-4-chlorobenzenesulfonamide 170 g of N-hexadecyl-3-nitro-4-chlorobenzenesulfonamide was dissolved in 640 ml of acetone, and 79 g of potassium carbonate, 6 ml of polyethylene glycol (average molecular weight: 400), and 71 g of dimethyl sulfate were added thereto, followed by refluxing the mixture for 5 hours under heating. 240 ml of acetone was added to the reaction solution, and 870 ml of water was further dropwise added thereto with stirring and keeping the temperature of the reaction solution at 40° C. Cooling the mixture to room temperature yielded crystals. The crystals were collected by filtration, washed in succession with water and methanol and then dried.

Yield: 169 g (97 %); mp: 74°–75 ° C.

Synthesis Example 1-4: Synthesis of 5-t-butyl-2-(4-N-methyl-N-hexadecylsulfamoyl-2-nitrophenyl)-4-isoxazolin-3-one 470 g of N-methyl-N-hexadecyl-3-nitro-4-chlorobenzenesulfonamide, 169 g of 5-t-butyl-3-hydroxyisoxazole, 168 g of potassium carbonate, and 1.2 liters of dimethylsulfoxide were mixed with each other and reacted for 6 hours. The reaction solution was poured into ice water, and the crystals which precipitated were collected by filtration, washed with water, then dried.

Yield: 576 g (100 %); mp: 67°–68 ° C.

Synthesis Example 1-5: Synthesis of 5-t-butyl-4-chloromethyl-2-(4-N-methyl-N-hexadecylsulfamoyl-2-nitrophenyl)-4-isoxazoline-3-one 550 g of 5-t-butyl-2-(4-N-methyl-N-hexadecylsulfamoyl-2-nitrophenyl)-4-isoxazoline-3-one, 200 g of zinc chloride, 200 g of paraformaldehyde, and 1.5 liters of acetic acid were mixed with each other, and the mixture was refluxed under heating for 10 hours while blowing hydrogen chloride gas thereinto in an amount of saturation. After being cooled, the reaction solution was poured into water, and the crystals which precipitated were collected by filtration and recrystallized from a mixed solvent of acetonitrile; methanol (1:4 vol.).

Yield: 585 g (96%); mp: 56° C.

Synthesis Example 1-6: Synthesis of Compound 9

250 g of 5-t-butyl-4-chloromethyl-2-(4-N-methyl-N-hexadecylsulfamoyl-2-nitrophenyl)-4-isoxazoline-3-one and 75 g of 1-phenyl-5-mercaptotetrazole were dissolved in 500 ml of acetone, 60 g of potassium carbonate was added thereto, and the resulting mixture was stirred at room temperature for 2 hours. The reaction mixture was poured into a dilute hydrochloric acid aqueous solution (1N), and the product was extracted with ethyl acetate. The extract was washed with water, dried, and concentrated under reduced pressure. One liter of ethanol and 100 ml of ethyl acetate were added to the residue to conduct recrystallization.

Yield: 250 g (82%); mp: 73°–75° C.

EXAMPLE 2

Synthesis of Compound 3:

Synthesis Example 2-1: Synthesis of N-methyl-N-octadecyl-3-nitro-4-chlorobenzamide 105.7 g of 3-nitro-4-chlorobenzoic acid and 800 ml of acetonitrile were mixed with each other, and 68.6 g of thionyl chloride was added thereto, followed by refluxing the mixture for 4 hours under heating. After cooling, the solvent was distilled off, and the residue was dissolved in chloroform. 63.5 g of triethylamine was added thereto, and the temperature was adjusted to 5° C. Then, a solution of 148.6 g of N-methyloctadecylamine in chloroform was dropwise added thereto. After completion of the reaction, water was added thereto. After separation, the organic phase was dried over anhydrous sodium sulfate. After removal of the inorganic substance (sodium sulfate) by filtration, the solvent was distilled off. The residue was recrystallized from acetonitrile-methanol (1:3 vol.).

Yield: 186 g (76.0%); mp: 55°–56° C.

Synthesis Example 2-2: Synthesis of 5-t-butyl-2-(4-N-methyl-N-octadecylcarbamoyl-2-nitrophenyl)-3-isoxazolone 300 ml of dimethylformamide was added to a mixture of 34.1 g of N-methyl-N-octadecyl-3-nitro-4-chlorobenzamide, 12.4 g of 5-t-butyl-3-hydroxyisoxazole, and 12.4 g of potassium carbonate, then reaction was conducted at 100° C. for 5 hours. After the reaction, the solvent was distilled off under reduced pressure, then ethyl acetate and water were added thereto, followed by stirring. The organic phase was separated, and the main product was isolated by silica gel column chromatography. The product was recrystallized from n-hexane-ethyl acetate.

Yield: 18.0 g (43.1%); mp: 64° C.

Synthesis Example 2-3: Synthesis of 4-chloromethyl-5-t-butyl-2-(4-N-methyl-N-octadecylcarbamoyl-2-nitrophenyl)-3-isoxazolone 36 g of 5-t-butyl-2-(4-N-methyl-N-octadecylcarbamoyl-2-nitrophenyl)-3-isoxazolone, 5.7 g of paraformaldehyde, and 10.3 g of zinc chloride were mixed with 250 ml of acetic acid, and reaction was conducted at 100° C. for 20 hours while blowing hydrogen chloride gas thereinto in an amount of saturation. After completion of the reaction, the reaction mixture was cooled and poured into ice water. The solids which precipitated were collected by filtration, dissolved in chloroform, and purified by silica gel column chromatography.

Yield: 10.0 g (25.6%); mp: 77° C.

Synthesis Example 2-4: Synthesis of Compound 3

The chloromethyl derivative synthesized in Synthesis Example 2-3 was reacted using the same procedure and molar ratios as employed in Synthesis Example 1-6 in Example 1, and the residue obtained by concentrating the extract was purified by column chromatography (developing solvent: ethyl acetate: hexane=1:2 vol.) and recrystallized from methanol.

Yield: 65%; mp: 64°–66° C.

EXAMPLE 3

Synthesis of Compound 14

Synthesis Example 3-1: Synthesis of 5-t-butyl-2-(4-dimethylsulfamoyl-2-nitrophenyl)isoxazolin-3-one 26.5 g of dimethyl 4-chloro-3-nitrobenzenesulfonamide and 17.0 g of 5-t-butyl-3-hydroxyisoxazole were dissolved in 100 ml of dimethylsulfoxide, 17 g of potassium carbonate was added thereto, and reaction was conducted for 7 hours at 65° C. After completion of the reaction, the reaction mixture was poured into cold dilute hydrochloric acid (1N). Upon stirring the mixture, crystals were precipitated. The crystals were collected by filtration and recrystallized from methanol to obtain the desired compound.

Yield: 33.1 g (89.5%); mp: 167°–168° C.

Synthesis Example 3-2: Synthesis of 5-t-butyl-4-chloromethyl-2-(4-dimethylsulfamoyl-2-nitrophenyl)-4-isoxazolin-3-one 11.8 g of 5-t-butyl-2-(4-dimethylsulfamoyl-2-nitrophenyl)-4-isoxazolin-3-one, 50 ml of acetic acid, 4.3 g of paraformaldehyde, and 6.5 g of zinc chloride were mixed with each other and refluxed for 5.5 hours under heating with blowing hydrogen chloride gas thereinto in an amount of saturation. After completion of the reaction, the solvent was distilled off under reduced pressure. Water and ethyl acetate were added to the residue to extract. The organic phase was washed twice with an aqueous solution of sodium bicarbonate and then the solvent in the organic phase was distilled off. The thus obtained oily product was subjected to silica gel column chromatography to obtain the desired end product.

Yield: 5.4 g (40.4%); mp: 163°–164° C.

Synthesis Example 3-3: Synthesis of Compound 14

5.0 g of 5-t-butyl-2-(4-dimethylsulfamoyl-2-nitrophenyl)-4-isoxazolin-3-one and 2.3 g of 1-phenyl-5mercaptotetrazole were dissolved in 50 ml of ethyl acetate, and 2 ml of triethylamine was added thereto at room temperature, followed by conducting reaction at room temperature for 2 hours. The reaction mixture was then poured into a dilute hydrochloric acid aqueous solution (1N), and the organic layer was separated out, washed with water, and concentrated. The residue was recrystallized from a mixed solvent of methanol and a small amount of water.

Yield: 5.1 g (76%); mp: 172°–173° C.

EXAMPLE 4

Synthesis of Compound 36

Synthesis Example 4-1: Synthesis of ethyl 4-chloro-3-nitrobenzoate 6.0 g of 4-chloro-3-nitrobenzoic acid and 17 ml of methanol were mixed with each other, and the mixture was stirred at room temperature. 0.6 ml of concentrated sulfuric acid was added thereto, and the mixture was refluxed for 4 hours under heating. After completion of the reaction, the reaction solution was cooled, and 17 ml of water was added thereto. The crystals formed were collected by filtration.

Yield: 6 g (93.5%)

Synthesis Example 4-2: Synthesis of 5-t-butyl-2-(4-isoxazolin-3-one 413.3 g of ethyl 4-chloro-3-nitrobenzoate, 305 g of 5-butyl-3-hydroxyisoxazole, and 1 liter of dimethylsulfoxide were mixed and stirred. 300 g of sodium bicarbonate was added thereto, and reaction was conducted at 90° C. for 8 hours. Then, the reaction mixture was cooled, and 1.5 liters of methanol and 3 liters of water were successively added thereto to precipitate crystals. The crystals were collected by filtration.

Yield: 560.7 g (93.2%); mp: 88° C.

Synthesis Example 4-3: Synthesis of 5-t-butyl-4-chloromethyl-2-(4-carboxy-2-nitrophenyl)-4-isoxazolin-3-one 300.9 g of 5-t-butyl-2-(4-ethoxycarbonyl-2-nitrophenyl)-4-isoxazoline-3-one, 191.1 g of paraformaldehyde, 191.1 g of zinc chloride, and 910 ml of acetic acid were mixed with each other, and reaction was conducted for 4 hours over a steam bath while blowing hydrogen chloride gas thereinto in an amount of saturation. Then, 500 ml of water was added thereto, and reaction was further conducted for 2 hours. Subsequently, 500 ml of concentrated hydrochloric acid was added thereto, and the mixture was further heated for 3 hours. Thereafter, heating was discontinued, and the reaction mixture was cooled to room temperature. The crystals which precipitated were collected by filtration, washed with water, and dried. The obtained end product began to melt at 217° C. and then gradually decomposed.

Yield: 319.3 g (96%); mp: 217° C. (decomposition)

Synthesis Example 4-4: Synthesis of 5-t-butyl-4-chloromethyl-2-(4-n-hexadecylcarbamoyl-2-nitrophenyl)-4-isoxazolin-3-one 81.6 g of 5-t-butyl-4-chloromethyl-2-(4-carboxy-2-nitrophenyl)-4-isoxazolin-3-one and 480 ml of ethyl acetate were mixed with each other, then cooled to −15° C. To this suspension was dropwise added 32.6 ml of triethylamine. Then, 22.0 ml of ethyl chlorocarbonate was dropwise added thereto while keeping the temperature of the mixture at not higher than −10° C.

After reacting under such conditions for 50 minutes, 49 g of hexadecylamine was added thereto. After reacting for 10 minutes at −10° C., the temperature of the reaction mixture was gradually raised to room temperature, and the mixture was left overnight. Then, 400 ml of water was added thereto, and the organic layer was separated and concentrated using an evaporator to dryness. The residue was crystallized from methanol.

Yield: 100.9 g (75.9%)

Synthesis Example 4-5: Synthesis of Compound 36

150 ml of acetone was added to a mixture of 30 g of 5-t-butyl-4-chloromethyl-2-(4-n-hexadecylcarbamoyl-2-nitrophenyl)-4-isoxazoline-3-one and 10.2 g of 1-phenyl-5-mercaptotetrazole and, after adding thereto 8 g of potassium carbonate, the mixture was stirred for 1 hour and 30 minutes at room temperature. The reaction solution was then poured into a dilute hydrochloric acid aqueous solution (1N), and extracted with ethyl acetate. The extract was washed with water and concentrated using an evaporator. The residue was recrystallized from 150 ml of a mixed solvent of ethyl acetate-methanol (1:5 vol.).

Yield 32 g (83%); mp: 68°–70° C.

EXAMPLE 5

Synthesis of Compound 43:

90 ml of acetone was added to a mixture of 17.7 g of 5-t-butyl-4-chloromethyl-2-(4-carboxy-2-nitrophenyl)-4-isoxazolin-3-one, 9.8 g of 1-phenyl-5-mercaptotetrazole, and 7.6 g of potassium carbonate, and the mixture was stirred for 3 hours at room temperature. The reaction solution was then poured into a dilute hydrochloric acid aqueous solution (1N), extracted with ethyl ester at high temperature (40° C.), and washed with warm water. The extract was cooled and, after precipitation of crystals, hexane was added thereto, followed by stirring at 0° C. and collecting the crystals by filtration.

Yield: 20 g (81%); mp: 179°–181° C.

EXAMPLE 6

Synthesis Example 6-1: Synthesis of 5-t-butyl-2-(4-nitro-2-N-methyl-N-octadecylsulfamoylphenyl)-4-isoxazolin-3-one 62 g of N-methyl-n-octadecyl 2-chloro-5-nitrobenzenesulfonamide, 220 ml of dimethylformamide, 20.9 g of 5-t-butyl-3-hydroxyisoxazole, and 20.7 g of potassium carbonate were mixed with each other and reacted at 80° C. for 6 hours. The reaction solution was acidified with hydrochloric acid, then dimethylformamide was distilled off. Water and ethyl acetate were added to the residue to extract the product.

The organic layer was purified by silica gel column chromatography to separate the desired end product.

Yield: 29 g (38.8%); mp: 55°–56° C.

Synthesis Example 6-2: Synthesis of 5-t-butyl-4-chloromethyl-2-(4-nitro-2-N-methyl-n-octadecylsulfamoylphenyl)-4-isoxazolin-3-one 20 g of 5-t-butyl-2-(4-nitro-2-N-methyl-N-octadecylsulfamoylphenyl)-4-isoxazolin-3-one, 100 ml of acetic acid, 3 g of paraformaldehyde, and 5.4 g of zinc chloride were mixed and refluxed for 7 hours under heating while blowing hydrogen chloride gas thereinto in amount of saturation. After completion of the reaction, the solvent was distilled off under reduced pressure, and the residue was dissolved in chloroform, and subjected to silica gel column chromatography to separate and obtain the desired end product.

Yield: 12.3 g (57.0%); mp: 48°–50° C.

Synthesis Example 6-3: Synthesis of Compound 52

100 ml of acetone was added to a mixture of 10 g of 5-t-butyl-4-chloromethyl-2-(4-nitro-2-N-methyl-N-octadecylsulfamoylphenyl)-4-isoxazolin-3-one, 2.7 g of 1-phenyl-5-mercaptotetrazole, 4 g of sodium hydrogen carbonate, and 0.1 g of sodium iodide, and the mixture was stirred for 4 hours at room temperature. The reaction solution was then poured into a dilute hydrochloric acid aqueous solution (1N), extracted with ethyl acetate and, after concentration, the residue was purified by silica gel column chromatography. The end product was obtained from a fraction of hexane-ethyl acetate (1:1 vol.).

Yield: 8.4 g (69%); mp: 53°–55° C.

EXAMPLE 7

Synthesis of Compound 51:

Synthesis Example 7-1: Synthesis of 5-methyl-2-(2-nitro-4-trifluoromethylphenyl)-4-isoxazolin-3-one 226 g of 4-chloro-3-nitrobenzotrifluoride, 129 g of 3-hydroxy-5-methylisoxazole, 336 g of sodium hydrogen carbonate, and 600 ml of dimethylsulfoxide were mixed with each other and reacted at 75° C. for 6 hours. After completion of the reaction, the reaction solution was poured into water, and the crystals which precipitated were purified using a silica gel short column chromatography and recrystallized from water-methanol.

Yield 176 g (61.1%); mp: 122° C.

Synthesis Example 7-2: Synthesis of 4-chloromethyl-5-methyl-2-(4-trifluoromethyl-2-nitrophenyl)-isoxazolin-3-one 165 g (0.573 mols) of 5-methyl-2-(4-trifluoromethyl-2-nitrophenyl)isoxazolin-3-one, 156.2 g of zinc chloride, 206.3 g of paraformaldehyde, and 5 ml of sulfuric acid were mixed with each other, and 400 ml of acetic acid was added thereto, followed by stirring the resulting mixture.

Hydrogen chloride gas was blown into this mixture at room temperature to saturation, and the mixture was refluxed under heating for 8 hours with continued blowing of the hydrogen chloride gas. After being cooled, the reaction solution was poured into ice water, and ethyl acetate was added thereto to extract. The extract was then evaporated to dryness, freed of colorants using a silica gel short column chromatography and, then recrystallized from n-hexane-ethyl acetate (=4:1 vol.).

Yield: 110 g (57%); mp: 68°–70° C.

Synthesis Example 7-3: Synthesis of Compound 51

The chloro derivative synthesized in Synthesis Example 7-2 was used, and was reacted by the same procedure and molar ratios as employed in Synthesis Example 1-6 in Example 1.

Recrystallization was conducted from n-hexaneethyl acetate (=5:1 vol.) to obtain the desired end product.

Yield: 77%; mp: 88°–90° C.

EXAMPLE 8

Synthesis of Compound 49:

Synthesis Example 8-1: Synthesis of 4-chloromethyl-5-phenyl-2-(4-carboxy-2-nitrophenyl)-isoxazolin-3-one 270 g (0.67 mols.) of 4-chloromethyl-5-phenyl-2-(4-ethoxycarbonyl-2-nitrophenyl)isoxazolin-3-one was added to 2.5 liters of 1,4-dioxane, and 300 ml of concentrated hydrochloric acid was added thereto, followed by refluxing the mixture for 8 hours under heating. After cooling, water was added to the reaction solution, and the crystals which precipitated were collected by filtration, washed with water, and dried.

Yield: 210.2 g (83.7%); mp: 186°–189° C.

Synthesis Example 8-2: Synthesis of 4-chloromethyl-5-phenyl-2-(4-(3-dodecyloxypropylcarbamoyl)-2-nitropropyl) isoxazolin-3-one 150 g (0.400 mols) of 4-chloromethyl-5-phenyl-2-(4-carboxy-2-nitrophenyl)isoxazolin-3-one and 600 ml of chloroform were mixed with each other, and 90.8 g of dicyclohexylcarbodiimide was added thereto, followed by reaction at room temperature for 30 minutes. Then, 97.4 g of 3-dodecyloxypropylamine was dropwise added thereto. After completion of the dropwise addition, the reaction was conducted for 5 hours. The reaction product was purified using a silica gel short column chromatography, then recrystallized from acetonitrile to obtain the desired end product.

Yield: 78.0 g (33.4%); mp: 110°–111° C.

Synthesis Example 8-3: Synthesis of Compound 49

The chloromethyl derivative synthesized in Synthesis Example 8-2 was used, and was reacted in the same molar ratios and by the same procedure as employed in Synthesis Example 1-6. The concentrated residue was subjected to silica gel flash column chromatography. The end product was obtained from a fraction of hexane-ethyl acetate (=3:1 vol.). Methanol was added to the purified product, and the solution was cooled to solidify the product.

Yield: 69%; mp: 40°–42° C.

EXAMPLE 9

Synthesis of Compound 61:

Synthesis Example 9-1: Synthesis of 5-t-butyl-2-(4-methanesulfonyl-2-tetradecyl-sulfonylphenyl)-4-isoxazolin-3-one 32 g of 4-methanesulfonyl-2-tetradecylsulfonylchlorobenzene, 20 g of 5-t-butyl-3-hydroxyisoxazole, 20 g of potassium carbonate, and 140 ml of dimethylsulfoxide were mixed and reacted at 80° C. for 4 hours. After completion of the reaction, the reaction mixture was poured into water, and was extracted with ethyl acetate. The organic layer was purified by silica gel column chromatography to obtain the end product as the desired product.

Yield: 20.0 g (50.8%); mp: 97°–98° C.

Synthesis Example 9-2: Synthesis of 5-t-butyl-4-chloromethyl-2-(4-methanesulfonyl-2-tetradecylsulfonylphenyl)-4-isoxazolin-3-one 13 g of 5-t-butyl-2-(4-methanesulfonyl-2-tetradecylsulfonylphenyl-4-isoxazolin-3-one, 3.2 g of paraformaldehyde, 4.8 g of zinc chloride, 3 ml of sulfuric acid, and 100 ml of acetic acid were mixed and refluxed for 7 hours under heating with blowing hydrogen chloride gas thereinto in an amount of saturation.

After being cooled, the reaction mixture was poured into water, extracted with ethyl acetate, and purified by silica gel column chromatography to obtain 11 g of the end product.

Yield: 77.7%; mp: 110°–111° C.

Synthesis Example 9-3: Synthesis of Compound 61

The chloromethyl derivative synthesized in Synthesis Example 9-2 was used, and was reacted by the same procedure as employed in Synthesis Example 3-3. The thus obtained residue was recrystallized from ethanol.

Yield: 92%; mp: 119°–122° C.

EXAMPLE 10

Synthesis of Compound 28:

Synthesis Example 10-1: Synthesis of N-methyl-N-hexadecyl-3-nitro-4-chlorobenzenesulfonamide 170 g of N-hexadecyl-3-nitro-4-chlorobenzenesulfonamide was dissolved in 640 ml of acetone, and 79 g of potassium carbonate, 4006 ml polyethylene glycol, and 71 g of dimethyl sulfate were added thereto, followed by refluxing the mixture for 5 hours under heating. Then, 240 ml of acetone was added thereto, and 870 ml of water was dropwise added thereto at 40° C. Upon cooling the mixture to room temperature, crystals were precipitated. The crystals were collected by filtration, washed with water and methanol successively, and then dried.

Yield: 169 g (97%); mp: 74°–75° C.

Synthesis Example 10-2: Synthesis of 5-methyl-2-(4-N-nitrophenyl)-4-isoxazolin-3-one 16 g of N-methyl-N-hexadecyl-3-nitro-4-chlorobenzenesulfonamide, 4.8 g of 5-methyl-3-hydroxyisoxazole, 6.4 g of sodium hydrogen carbonate, and 50 ml of dimethylsulfoxide were mixed and reacted at 75° C. for 6 hours. The reaction solution was poured into a hydrochloric acid acidified ice water. The crystals which precipitated were collected by filtration, washed with water, recrystallized from methanol, and then dried.

Yield: 17.9 g (99%); mp: 63°–65° C.

Example 10-3: Synthesis of 5-methyl-4-chloromethyl-2-(4-N-methyl-N-hexadecylsulfamoyl-2-nitrophenyl)-4-isoxazolin-3-one 16 g of 5-methyl-2-(4-N-methyl-N-hexadecylsulfamoyl-2-nitrophenyl)-4-isoxazolin-3-one, 5 g of zinc chloride, 7 g of paraformaldehyde, 50 ml of acetic acid, and 0.5 ml of concentrated sulfuric acid were mixed and stirred at 75° C. for 9 hours while blowing hydrogen chloride gas thereinto in an amount of saturation. After being cooled, the reaction solution was poured into water and the crystals which precipitated were collected by filtration and recrystallized from methanol.

Yield: 16.3 g (94%); mp: 55°–56° C.

Synthesis Example 10-4: Synthesis of Compound 28

13 g of the chloromethyl derivative synthesized in Synthesis Example 10-3, 3.9 g of 1-phenyl-5-mercaptotetrazole, and 27 ml of acetone were charged and stirred to dissolve. Then, 3.2 g of potassium carbonate and 0.1 g of potassium iodide were added thereto, and reaction was conducted for 2 hours at room temperature. After completion of the reaction, 18.5 ml of ethyl acetate and 34 ml of n-hexane were added thereto and, while cooling with water, 30 ml of a dilute hydrochloric acid aqueous solution (1N) was dropwise added thereto, followed by separation at 40° C. The organic layer was taken up, and 60 ml of methanol was added thereto. Upon cooling the solution, crystals were precipitated.

Yield: 13 g (81%); mp: 81°–82° C.

EXAMPLE 11

Synthesis of Compound 33:

Synthesis Example 11-1: Synthesis of N,N-dibutyl-3-nitro-4-chlorobenzenesulfonamide 150 g of sodium hydroxide was dissolved in 200 ml of water, and the solution was cooled. To this solution was added 600 ml of dibutylamine, and the solution was cooled to 0° C. A solution of 954 g of 3-nitro-4-chlorobenzenesulfonyl chloride in 950 ml of acetonitrile was dropwise added thereto under vigorous stirring while keeping the solution temperature at not higher than 10° C. After completion of the dropwise addition, the reaction mixture was stirred for 1 hour at 10° C., and the crystals which precipitated were collected by filtration, washed wellwith a dilute hydrochloric acid aqueous solution (1N), and dried.

Yield: 1171 g (90%)

Synthesis Example 11-2: Synthesis of 5-methyl-2-(4-N, N-dibutyl -2-nitrophenyl) -4-isoxazoline-3-one 30 ml of dimethylsulfoxide was added to a mixture of 11 g of N,N-dibutyl-3-nitro-4-chlorobenzenesulfonamide, 5 g of 5-methyl-3-hydroxyisoxazole, and 6.3 g of sodium hydrogen carbonate, and reaction was conducted at 85° C. for 4 hours. After cooling the reaction solution to 40° C., 20 ml of isopropyl alcohol was added to the solution and, after filtration, the temperature of the filtrate was adjusted to 50° C. Then, 20 ml of water and 0.5 ml of hydrochloric acid were added thereto. Upon cooling, the crystals which formed were collected by filtration, washed with water, and dried.

Yield: 11.5 g (89%)

Synthesis Example 11-3: Synthesis of 5-methyl-4-chloromethyl-2-(4-N,N-dibutylsulfamoyl-2-nitrophenyl)-4-isoxazolin-3-one 35 ml of acetic acid was added to a mixture of 10.5 g of 5-methyl-2-(4-N,N-dibutylsulfamoyl-2-nitro-phenyl)-4-isoxazolin-3-one, 6.5 g of paraformaldehyde, and 4.5 g of zinc chloride and, further, 0.3 ml of sulfuric acid was added thereto. The mixture was stirred at 80° C. for 5 hours while blowing hydrogen chloride gas thereinto in amount of saturation. The reaction solution was added to 80 ml of 0° C. methanol, and 20 ml of ice water was added thereto. The crystals which precipitated were collected by filtration and dried.

Yield: 8.6 g (73%)

Synthesis Example 11-4: Synthesis of Compound 33

30 g of the chloromethyl derivative synthesized in Synthesis Example 11-3 and 11.6 g of 1-phenyl-5-mercaptotetrazole were dissolved in 100 ml of acetonitrile. Then, 10 g of potassium carbonate was added thereto, and the mixture was stirred at room temperature for 2 hours. The reaction solution was poured into a dilute hydrochloric acid aqueous solution (1N) and extracted with ethyl acetate. The extract was concentrated using an evaporator and recrystallized from methanol.

Yield: 33 g (84 %); mp: 122°–123 ° C.

EXAMPLE 12

Synthesis of Compounds 11 and 12

30 g of 5-t-butyl-4-chloromethyl-2-(N-methyl-N-hexadecylsulfamoyl-2-nitrophenyl)-4-isoxazolin-3-one and 7.73 g of compound A* described below were dissolved in 100 ml of acetone. Then, 7.25 g of potassium carbonate and 1 g of sodium iodide were added thereto, and the mixture was refluxed for 1 hour under heating.

After filtration, the filtrate was concentrated using an evaporator and subjected to silica gel column chromatography to obtain Compound 11 from a fraction of hexane-ethyl acetate (5:1 vol.) and Compound 12 from a fraction of hexane-ethyl acetate (3:1 vol.). The products were respectively recrystallized from methanol Yield: Compound 11: 7.4 g (21 %); mp: 80°–81 ° C.; Compound 12: 22 g (62%); mp: 94°–96 ° C.

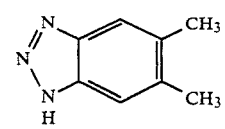

Compound A*

EXAMPLE 13

Synthesis of Compound 15:

50 ml of acetone was added to a mixture of 10 g of 5-t-butyl-4-chloromethyl-2-(N-methyl-N-hexadecylsulfamoyl-2-nitrophenyl)-4-isoxazolin-3-one, 2.88 g of compound B* described below, and 2.5 g of potassium carbonate, and reaction was conducted at room temperature for 1 hour. The reaction solution was poured into a dilute hydrochloric acid aqueous solution (1N) and extracted with ethyl acetate. The extract was then concentrated using an evaporator and crystallized from methanol.

Yield: 12 g (100 %); mp. 65°–66 ° C.

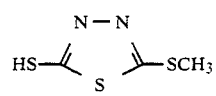

Compound B*

EXAMPLE 14

Synthesis of Compound 16:

Compound C* described below was subjected to the same procedure as in Example 13 to obtain the desired end product.

Yield: 92 %; mp: 81°–82 ° C.

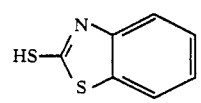

Compound C*

EXAMPLE 15

Synthesis of Compound 17:

Compound D* described below was subjected to the same procedure as in Example 13 to obtain the desired end product.

Yield: 75 %; mp: 93°–95 ° C.

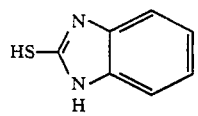
Compound D*

EXAMPLE 16

Compound E* was subjected to the same procedures as in Example 13, and the product was purified by silica gel chromatography and cooled in methanol for several days to obtain crystals.

Yield: 80 %; mp: 107°–108 ° C.

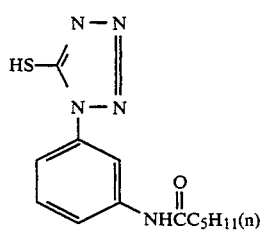
Compound E*

EXAMPLE 17

Synthesis of Compound 19

Compound F* was subjected to the same procedure as in Example 13 to obtain the desired end product.

Yield: 88 %; mp: 91°–93 ° C.

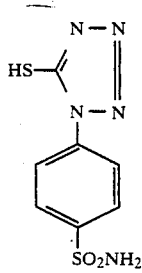
Compound F*

EXAMPLE 18

Synthesis of Compound 21:

Compound G* was subjected to the same procedure as in Example 12 to obtain the end product.

Yield: 85 %; mp: 96°–98 ° C.

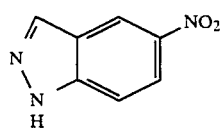
Compound G*

EXAMPLE 19

Synthesis of Compound 23

Compound H* was subjected to the same procedures as in Example 13, and the product was recrystallized from a mixed solvent of methanol-water (10:1 vol.).

Yield: 42 %; mp: 83°–85 ° C.

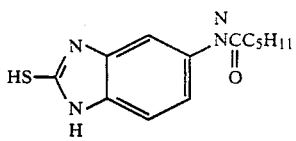
Compound H*

EXAMPLE 20

Synthesis of Compound 25:

3.7 g of Compound I* and 10 g of 5-t-butyl-4-chloromethyl-2-(N-methyl-N-hexadecylsulfamoyl-2-nitrophenyl)-4-isoxazoline-3-one were dissolved in 50 ml of acetonitrile, and the resulting solution was refluxed for 10 hours under heating. After removal of the solvent, methanol was added to the residue and, after heating to dissolve, the solution was left for several days at 0° C. The crystals which precipitated were collected by filtration.

Yield: 4.4 g (34 %); mp: 60°–61 ° C.

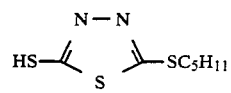
Compound I*

While the present invention has been described in detail and with reference to specific embodiments thereof, it is apparent to one skilled in the art that various changes and modifications can be made therein without departing from the spirit and the scope of the present invention.

What is claimed is:

1. 2-Aryl-4-isoxazoline-3-one derivatives having the following formula (I):

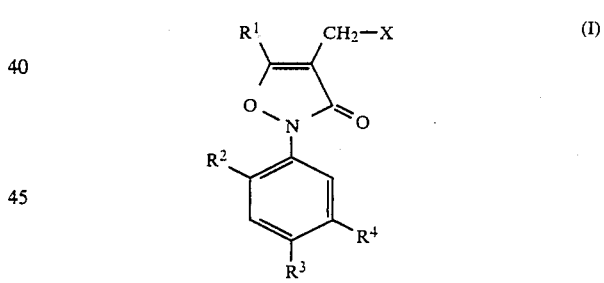

wherein $R^1$ represents an alkyl group containing 1 to 6 carbon atoms or an aryl group containing 6 to 24 carbon atoms, $R^2$, $R^3$, and $R^4$ each represents a hydrogen atom, a trifluoromethyl group, a carbamoyl group, a sulfonyl group, an alkoxycarbonyl group, an aryloxycarbonyl group, a sulfonyl group, a halogen atom, a cyano group, a nitro group, an alkoxy group, an aryloxy group, an acyl a carboxy group or a sulfo group, with at least one of $R^2$, $R^3$, and $R^4$ being selected from a nitro group, a cyano group, a sulfamoyl group, a carbamoyl group, and a sulfonyl group, and X represents a monovalent group from mercaptoazole, a mercaptoazaindene, a tetrazaindene, a mercaptopyrimidine, a benzotriazole, and indazole, and a benzimidazole, and wherein said alkoxy group, acyl group, alkoxycarbonyl group, aryloxycarbonyl group, and sulfonyl group contain not more than 20 carbon atoms, and said carbamoyl group and sulfamoyl group contain not more than 36 carbon atoms.

2. The compounds as claimed in claim 1, wherein X represents:
a 1-phenyl-5-tetrazolylthio group;
a 1-(4-carboxyphenyl)-5-tetrazolylthio group;
a 1-(3-hydroxyphenyl)-5-tetrazolylthio group;
a 1-(4-sulfophenyl)-5-tetrazolylthio group;
a 1-(3-sulfophenyl)-5-tetrazolylthio group;
a 1-(4 sulfamoylphenyl)-5-tetrazolylthio group;
a 1-(3-hexanoylaminophenyl)-5-tetrazolylthio group;
a 1-(3-nonanoylaminophenyl)-5-tetrazolylthio group;
a 1-(3-aminophenyl)-5-tetrazolylthio group;
a 1-(1-naphthyl)-5-tetrazolylthio group;
a 1-(3-(3-methylureido)phenyl)-5-tetrazolylthio group;
a 1-(4-nitrophenyl)-5-tetrazolylthio group;
a 1-(3-phenoxycarbonylphenyl)-5-tetrazolylthio group;
a 1-(4-phenoxycarbonylphenyl)-5-tetrazolylthio group;
a 1-(3-maleinimidophenyl)-5-tetrazolylthio group;
a 1-ethyl-5-tetrazolylthio group;
a 1-(2-carboxyethyl)-5-tetrazolylthio group;
a 1-(4-benzoyloxyphenyl)-5-tetrazolylthio group;
a 1-(3-vinylcarbonylphenyl)-5-tetrazolylthio group;
a 2-methylthio-5-(1,3,4-thiadiazolyl)thio group;
a 2-penthylthio-5-(1,3,4-thiadiazolyl)thio group;
a 2-(2-carboxyethylthio)-5-(1,3,4-thiadiazolyl)thio group;
a 2-(2-dimethylaminoethylthio)-5-(1,3,4-thiadiazolyl)thio group;
a 2-phenoxycarbonylmethylthio-5-(1,3,4-thiadiazolyl)thio group;
a 2-(3-(thiophen-2-ylcarbonyl)propyl)thio-5-(1,3,4-thiadiazolyl)thio group;
a 2-benzothiazolylthio group;
a 5-(2-methanesulfonylethoxycarbonyl)-2-benzothiazolylthio group;
a 2-benzimidazolylthio group;
a 1-(4-n-hexylcarbamoylphenyl)-2-imidazolylthio group;
a 1-phenyl-2-imidazolylthio group;
a 5-(2-ethylhexanoylamino)-2-benzimidazolylthio group;
a 5-hexanoylamino-2-benzimidazolylthio group;
a 5-phenoxycarbonyl-2-benzimidazolylthio group;
a 1-(4-(2-chloroethoxycarbonyl)phenyl)-2-imidazolylthio group;
a 2-benzoxazolylthio group;
a 2-(6-nitro-1,3-benzoxazolyl)thio group;
a 6-phenoxycarbonyl-2-benzoxazolylthio group;
a 3-methyl-4-phenyl-5-(1,2,4-triazolyl)thio group;
a 3-acetylamino-4-methyl-5-(1,2,4-triazolyl)thio group;
a 2-phenyl-5-(1,3,4-oxadiazoyl)thio group;
a 6-methyl-4-(1,3,3a,7-tetrazaindenyl)thio group;
a 6-methyl-2-benzyl-4-(1,3,3a,7-tetrazaindenyl)thio group;
a 6-phenyl-4-(1,3,3a,7-tetrazaindenyl)thio group;
a 4,6-dimethyl-2-(1,3,3a,7-tetrazaindenyl)thio group;
a 2-pyrimidinylthio group;
a 4-methyl-6-hydroxy-2-pyrimidinylthio group;
a 4-propyl-2-pyrimidinylthio group;
a benzotriazolyl group;
a 5-nitrobenzotriazolyl group;
a 5-methylbenzotriazolyl group;
a 5,6-dichlorobenzotriazolyl group;
a 5-bromobenzotriazolyl group;
a 5-methoxybenzotriazolyl group;
a 5-acetylaminobenzotriazolyl group;
a 5,6-dimethylbenzotriazolyl group;
a 5-n-butylbenzotriazolyl group;
a 5-nitro-6-chlorobenzotriazolyl group;
a 4,5,6,7-tetrachlorobenzotriazolyl group;
a 5-phenoxycarbonylbenzotriazolyl group;
a 5-(2,3-dichloropropyloxycarbonyl)benzotriazolyl group;
a 5-benzyloxycarbonylbenzotriazolyl group;
a 5-(butylcarbamoylmethoxycarbonyl)benzotriazolyl group;
a 5-(butoxycarbonylmethoxycarbonyl)benzotriazolyl group;
a 5-succinimidomethylbenzotriazolyl group;
an indazolyl group;
a 5-nitroindazolyl group;
a 3-nitroindazolyl group;
3-chloro-5-nitroindazolyl group;
a 3-cyanoindazolyl group;
a 3-n-butylcarbamoylindazolyl group;
a 5-nitro-3-methanesulfonylindazolyl group;
a 5-nitro-3-phenoxycarbonylindazolyl group;
a 5-nitrobenzimidazolyl group;
a 4-nitrobenzimidazolyl group;
a 5,6-dichlorobenzimidazolyl group;
a 5-cyano-6-chlorobenzimidazolyl group; or
a 5-trifluoromethyl-6-chlorobenzimidazolyl group.

3. The compounds as claimed in claim 1, wherein X represents:
a 1-phenyl-5-tetrazolythio group;
a 2-methyl-thio-5-(1,3,4-thiadiazolyl)thio group;
a 2-benzothiazolythio group;
a 2-benzimidazolythio group;
a 5-nitrobenzotriazolyl group; or
a 6-methylbenzotriazolyl group.

4. The compounds as claimed in claim 1, wherein $R^1$ in general formula (I) is a methyl group or a t-butyl group.

5. The compounds as claimed in claim 1, wherein $R^1$ in general formula (I) is an aryl group or an aryl group substituted with an alkoxy group or a sulfo group.

6. The compounds as claimed in claim 1, wherein $R^1$ in general formula (I) is a phenyl group, a 4-methoxyphenyl group, a 4-hexadecyloxyphenyl group or a 3-sulfo-4-methoxyphenyl group.

7. The compounds as claimed in claim 1, wherein at least one of $R^2$ and $R^3$ in general formula (I) is a nitro group.

8. The compounds as claimed in claims 1, wherein $R^2$ and $R^3$ in general formula (I) each represents a group selected from among a trifluoromethyl group, a cyano group, and a sulfonyl group.

9. The compounds as claimed in claim 6, wherein at least one of $R^2$, $R^3$, and $R^4$ is a group selected from a sulfonyl group, a sulfamoyl group, an alkoxycarbonyl group, a carbamoyl group, an acyl group, a trifluoromethyl group, a cyano group, a carboxy group, and a sulfo group.

10. The compounds as claimed in claim 7, wherein at least one of $R^2$, $R^3$, and $R^4$ is selected from a sulfonyl group, a sulfamoyl group, an alkoxycarbonyl group, a carbamoyl group an acyl group, a trifluoromethyl group, a cyano group, a carboxyl group, and a sulfo group.

11. The compounds as claimed in claim 1, wherein $R^2$ in general formula (I) is a nitro group, $R^3$ is a group selected from a sulfamoyl group, a carbamoyl group, an alkoxycarbonyl group, a trifluoromethyl group, a carboxy group, and a sulfo group, and $R^4$ is a hydrogen atom.

12. The compounds as claimed in claim 11, wherein X in general formula (I) is a 1-phenyl-5-tetrazolylthio group, a 2-methyl-thio-5-(1,3,4-thiadiazolylthio group, a 2-benzothiazolylthio group or a 2-benzimidazolylthio group.

13. The compounds as claimed in claim 11, wherein X in general formula (I) is a 1-phenyl-5-tetrazolylthio group.

14. The compounds as claimed in claim 12, wherein $R^3$ is a sulfamoyl group selected from a methylsulfamoyl group, a dimethylsulfamoyl group, a diethylsulfamoyl group, a dibutylsulfamoyl group, an N-methyl-N-n-hexylsulfamoyl group, an N-methyl-N-n-octylsulfamoyl group, an N-methyl-N-n-hexadecylsulfamoyl group, an N-methyl-N-n-octadecylsulfamoyl group, a n-dodecylsulfamoyl group, an N-phenyl-n-hexadecylsulfamoyl group, an N-methyl-N-3-methoxypropylsulfamoyl group, a bis(2-methoxyethyl)sulfamoyl group, and $$-SO_2N\underset{\diagdown\diagup}{\diagup\diagdown}O \text{ group};$$

a carbamoyl group selected from group, a dimethylcarbamoyl group, a diethylcarbamoyl group, a n-butylcarbamoyl group, a 3-(2,4-di-t-pentylphenoxy)propylcarbamoyl group an N-methyl-N-n-octylcarbamoyl group, a (3-hexadecylsulfamoyl)phenylcarbamoyl group, an N-methyl-N-n-octadecylcarbamoyl group, a n-hexadecylcarbamoyl group, a 3-n-dodecyloxypropylcarbamoyl group, and a carbamoyl group; or an alkoxycarbonyl group selected from a methoxycarbonyl group, an ethoxycarbonyl group, a n-octyloxycarbonyl group and a n-hexadecyloxycarbonyl group.

15. The compounds as claimed in claim 1, wherein $R^2$ in general formula (I) is a nitro group, a methylsulfonyl group, a n-tetradecylsulfonyl group, a dihexylsulfamoyl group, an N-methyl-N-n-octadecylsulfamoyl group or a sulfo group.

16. The compounds as claimed in claim 1, wherein $R^3$ in general formula (I) is a group selected from a nitro group, a trifluoromethyl group, a carboxy group, a sulfo group, a methylsulfonyl group, a dimethylsulfamoyl group, a diethylsulfamoyl group, a dibutylsulfamoyl group, a dioctylsulfamoyl group, an N-methyl-N-n-octylsulfamoyl group, an N-methyl-N-n-hexadecylsulfamoyl group, an N-methyl-N-n-octadecylsulfamoy l group, $$-SO_2N\underset{\diagdown\diagup}{\diagup\diagdown}O \text{ group},$$

a bis(2-methoxyethyl)sulfamoyl group, an ethoxycarbonyl group, a n-hexadecylcarbamoyl group, an N-methyl-N-n-octadecylcarbamoyl group and a 3-n-dodecyloxypropylcarbamoyl group.

17. The compounds as claimed in claim 1, wherein $R^4$ is a group selected from a hydrogen atom, a trifluoromethyl group and a n-hexadecyloxy group.

18. The compound as claimed in claim 1, said compound is a compound of the formula

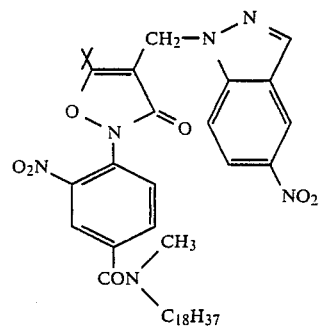

1

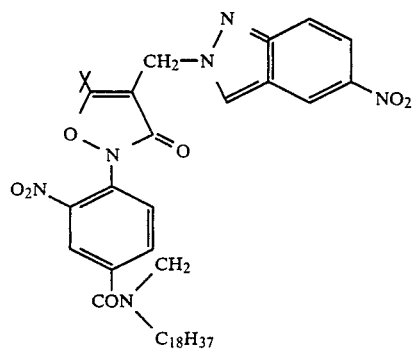

2

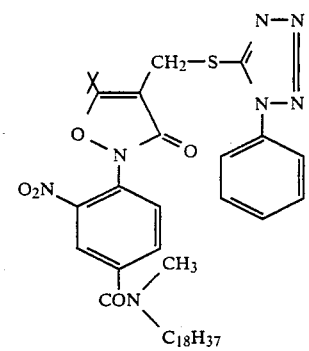

3

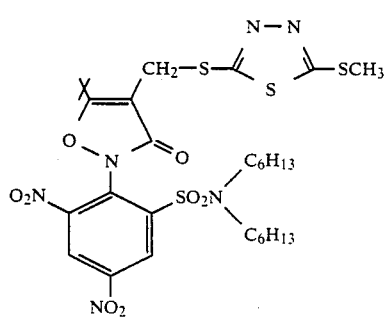

4

-continued
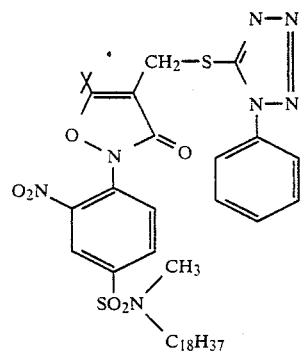
5
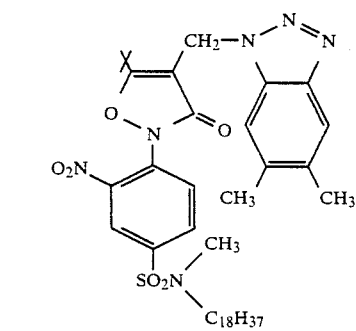
6
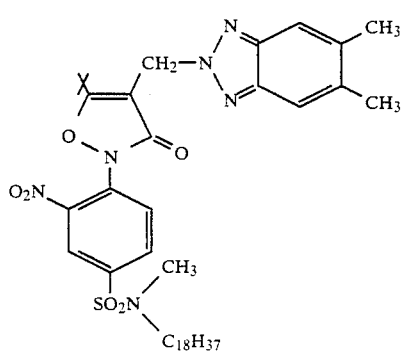
7
8
-continued
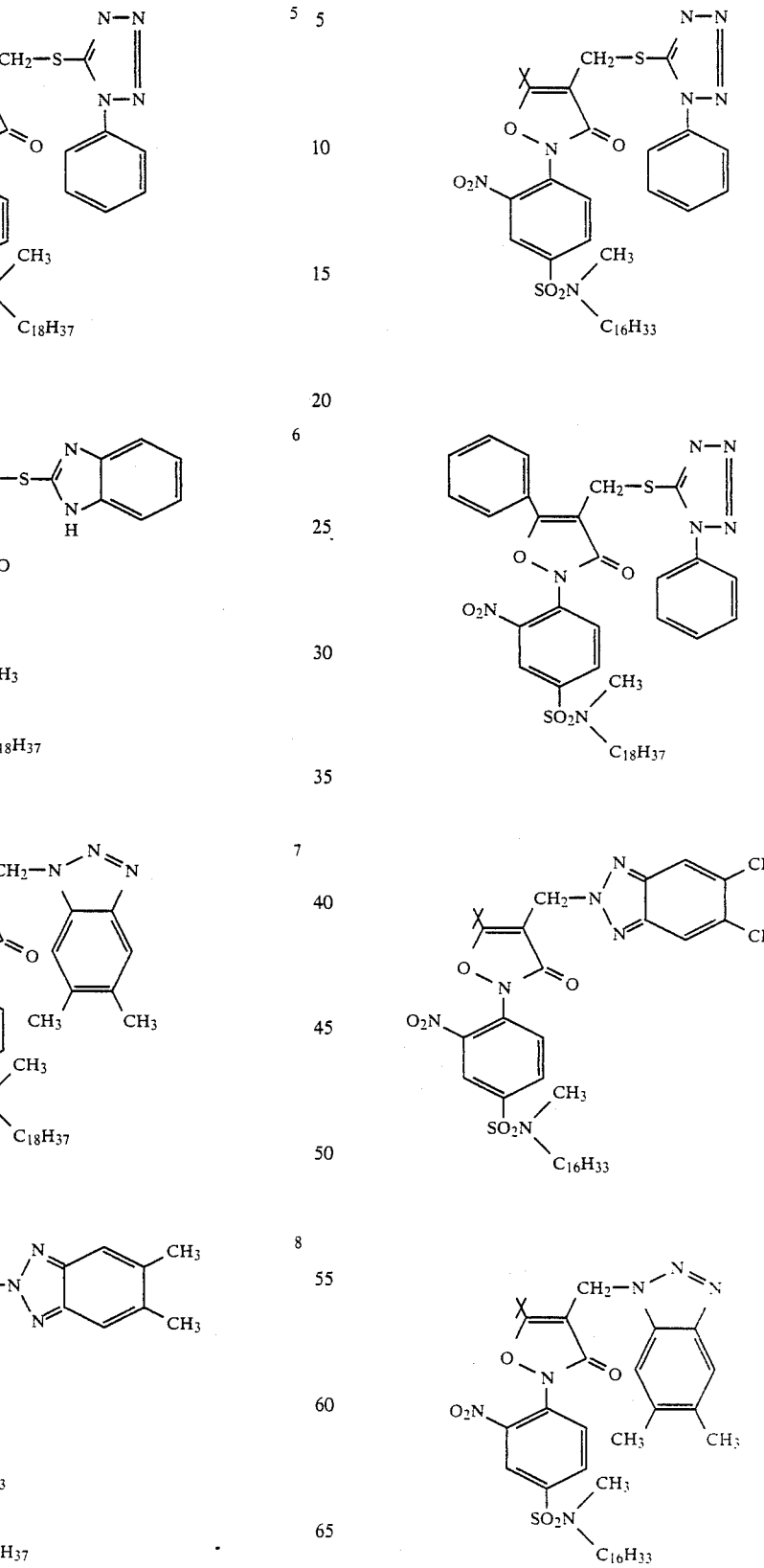
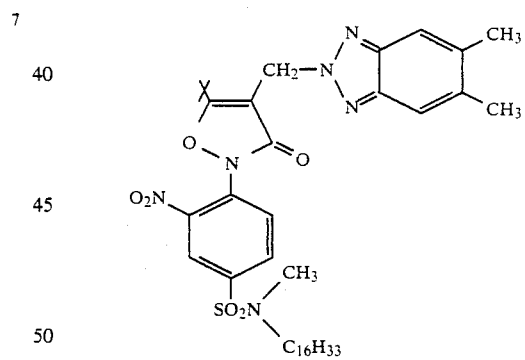

-continued

-continued
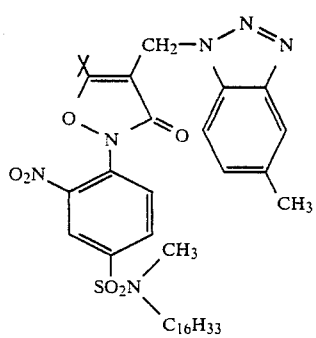
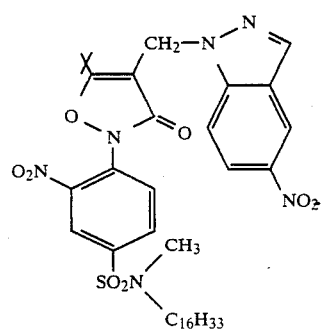
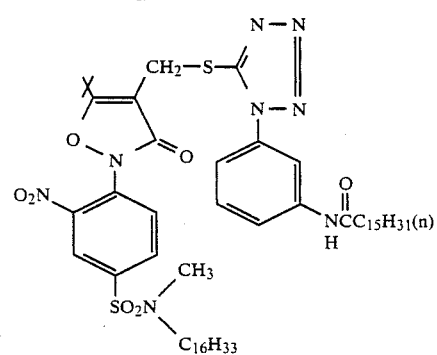
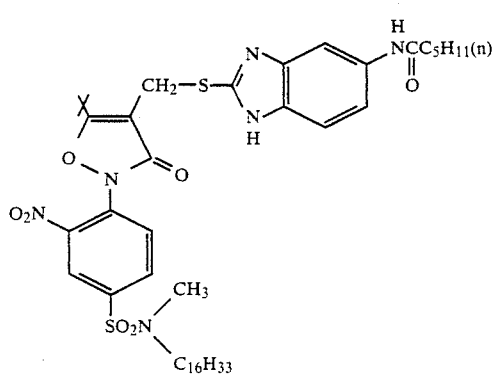
-continued
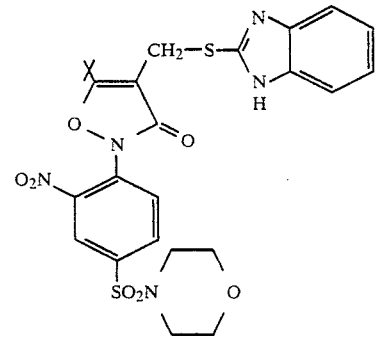
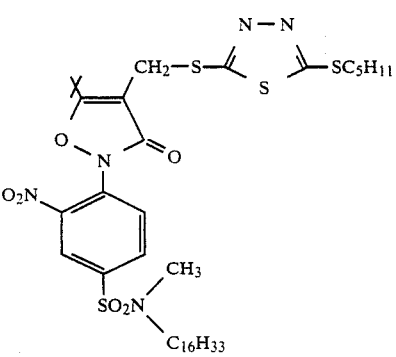
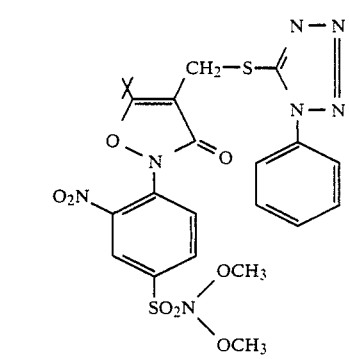
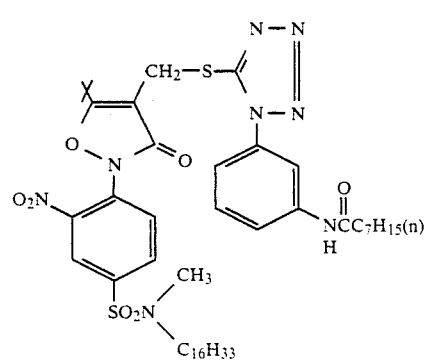

-continued
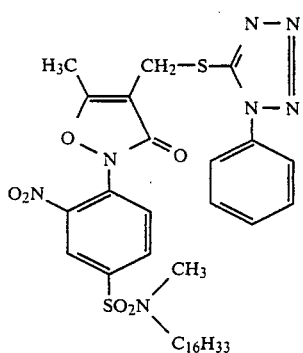 28
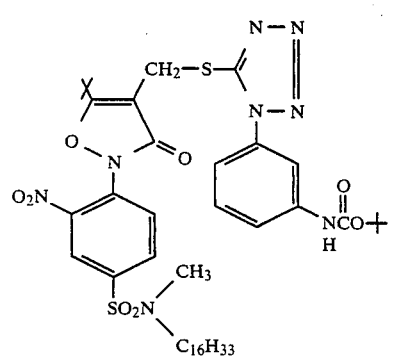 29
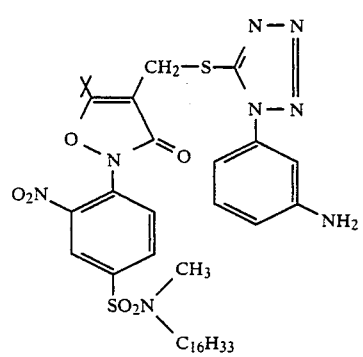 30
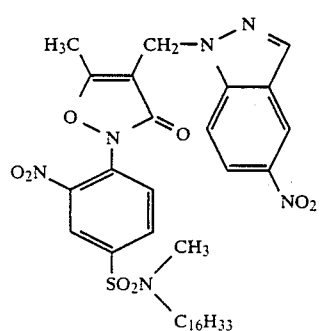 31
-continued
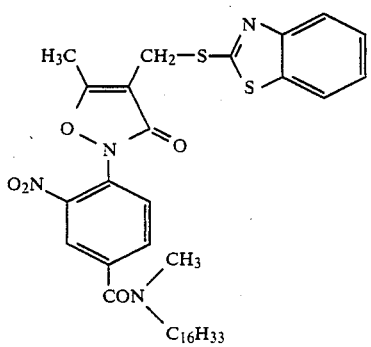 32
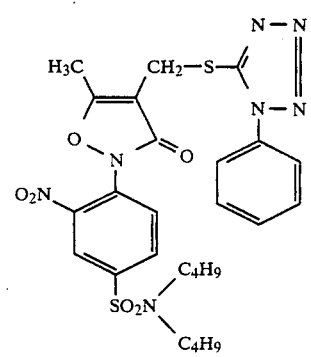 33
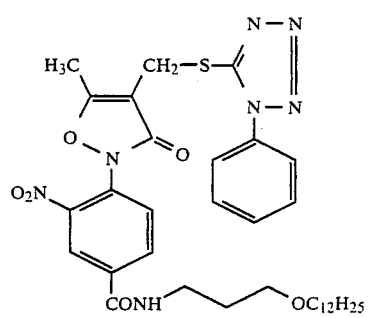 34
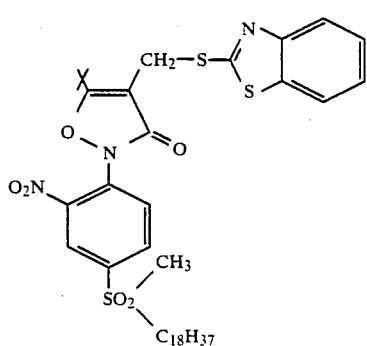 33

-continued
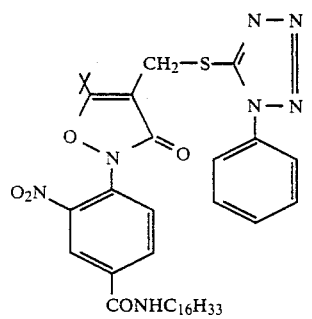 36
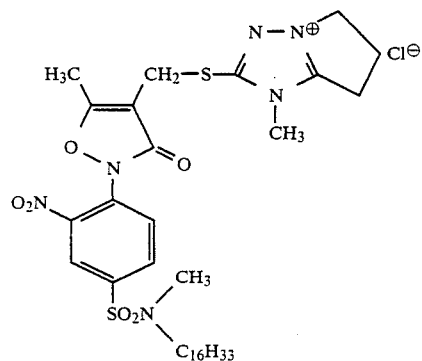 37
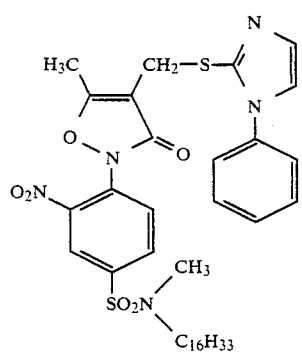 38
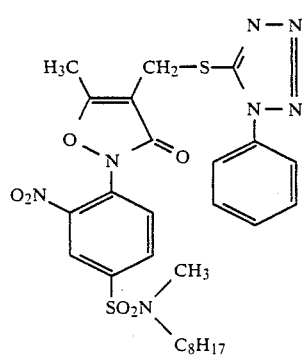 39
-continued
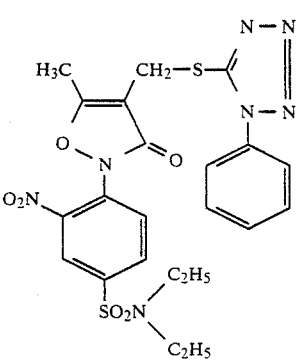 40
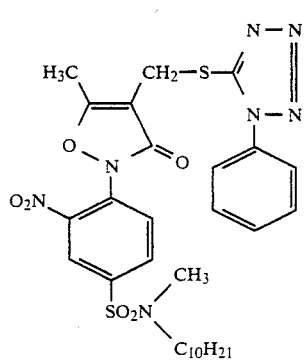 41
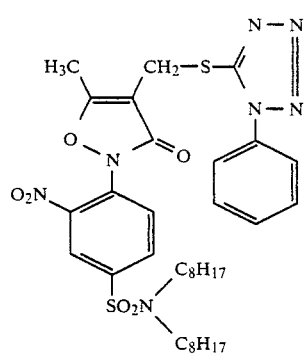 42
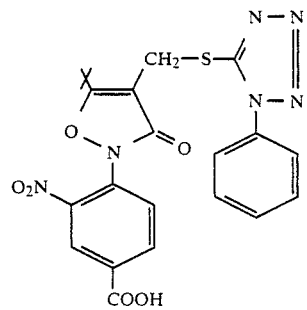 43

-continued
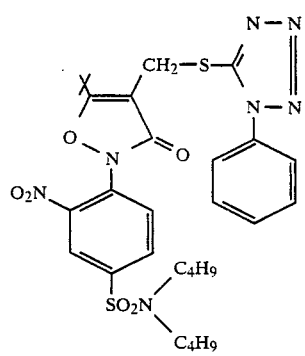 44
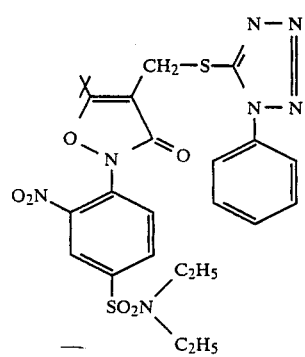 45
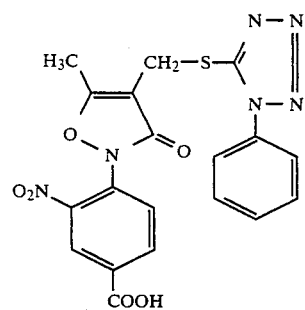 46
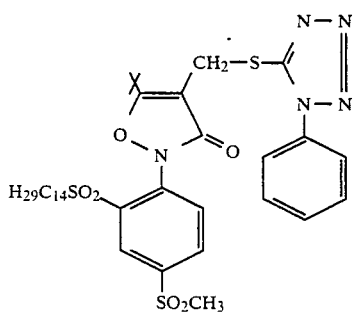 47
-continued
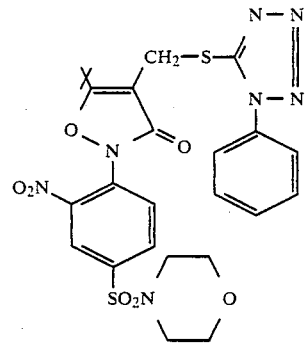 48
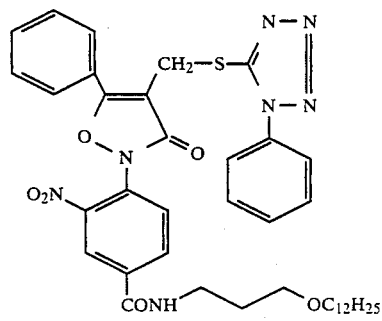 49
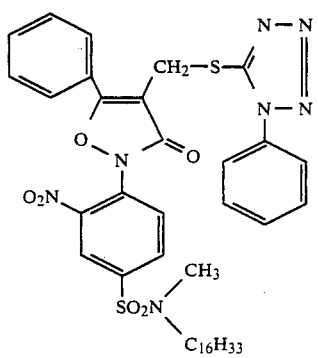 50
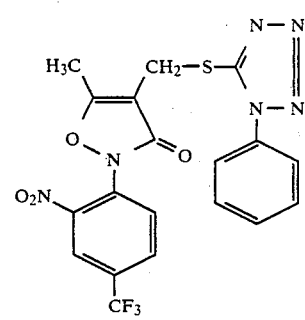 51
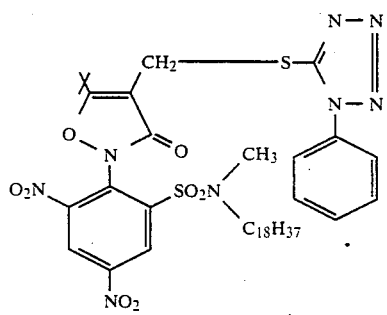 52

-continued
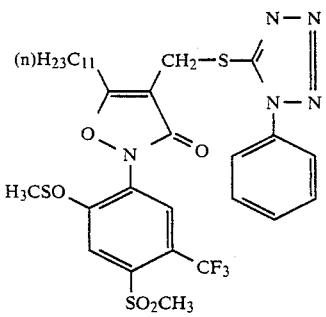
53
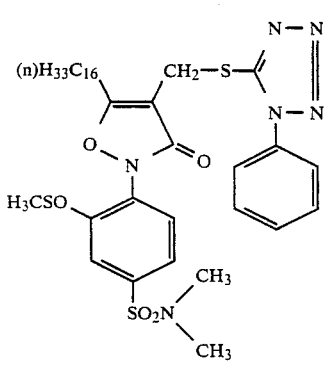
54
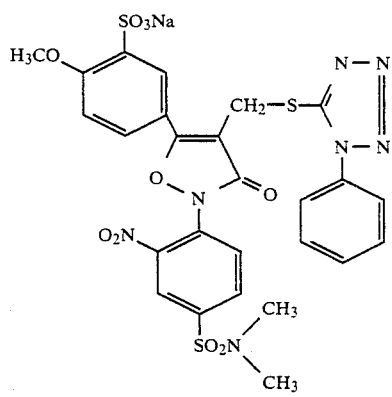
55
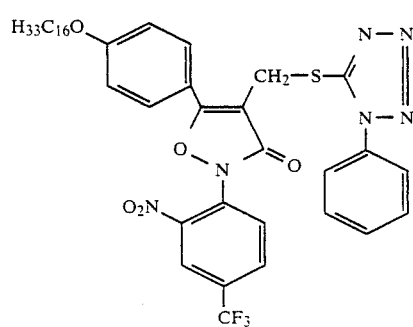
56
-continued
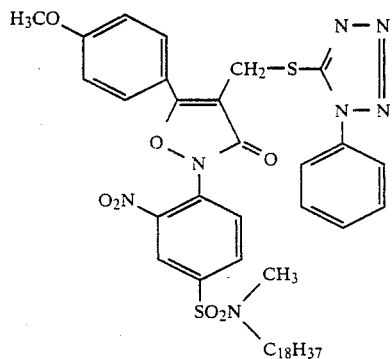
57
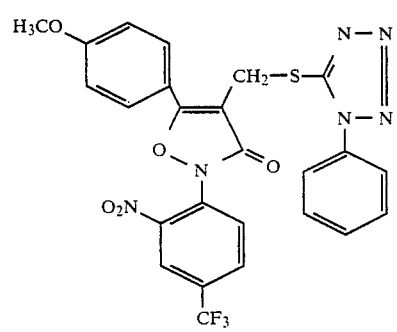
58
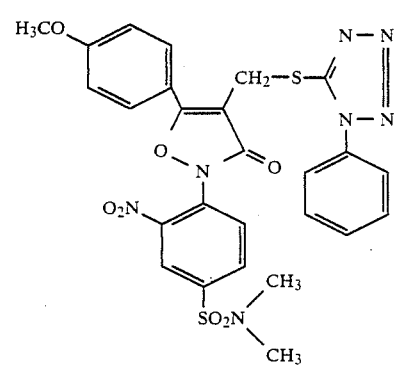
59
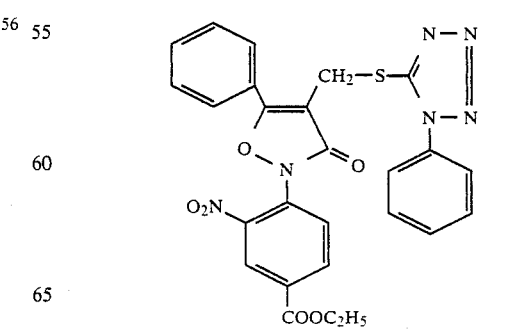
60

-continued
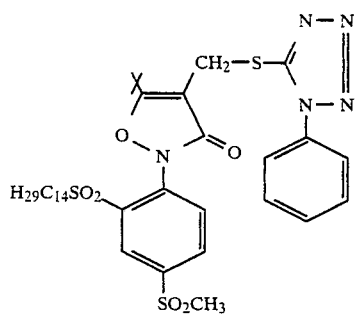
61
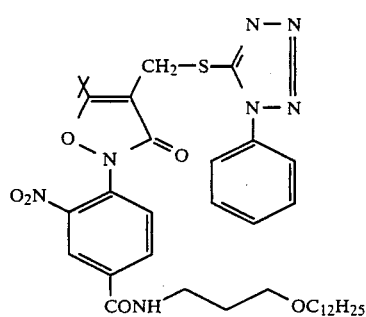
62
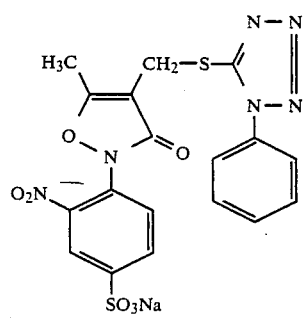
63
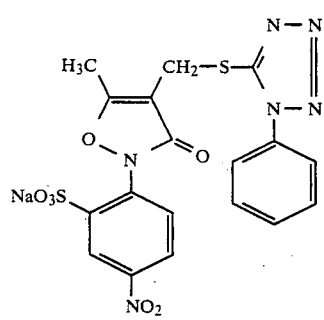
64
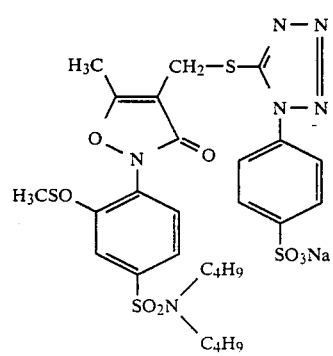
65
-continued
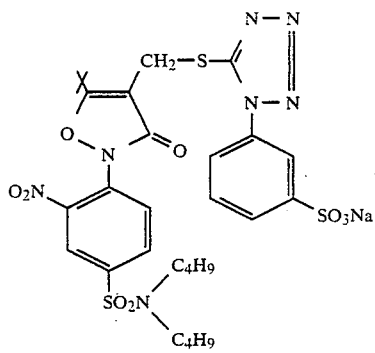
66
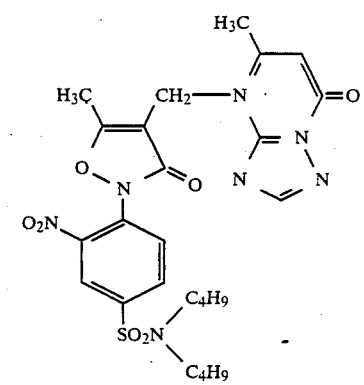
68
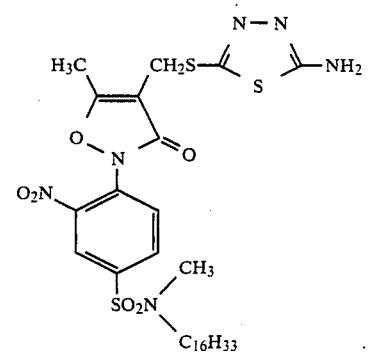
69
19. The compound as claimed in claim 1, said compound is a compound of the formula
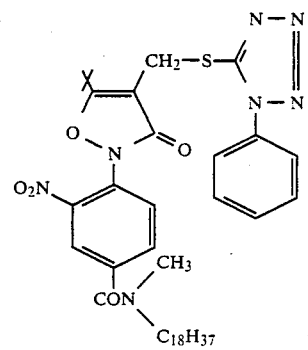
3

-continued
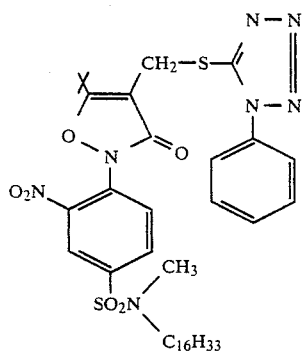 9
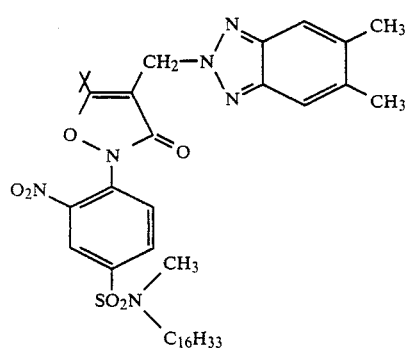 11
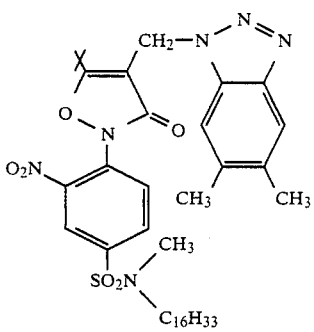 12
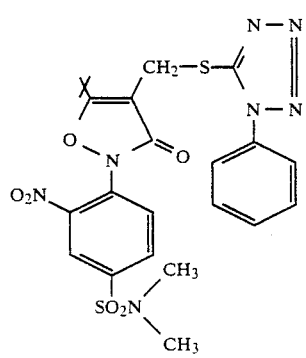 14
-continued
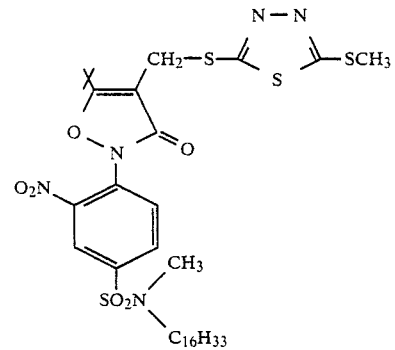 15
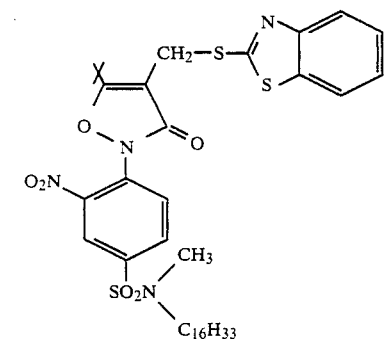 16
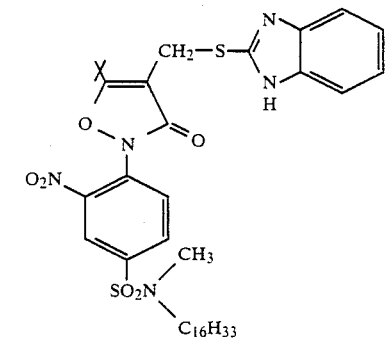 17
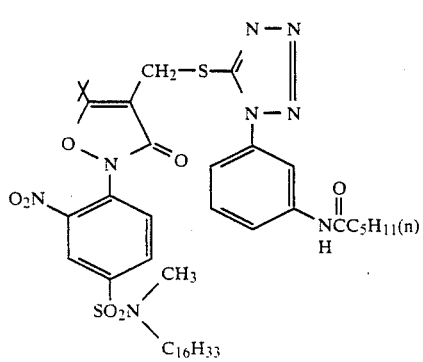 18

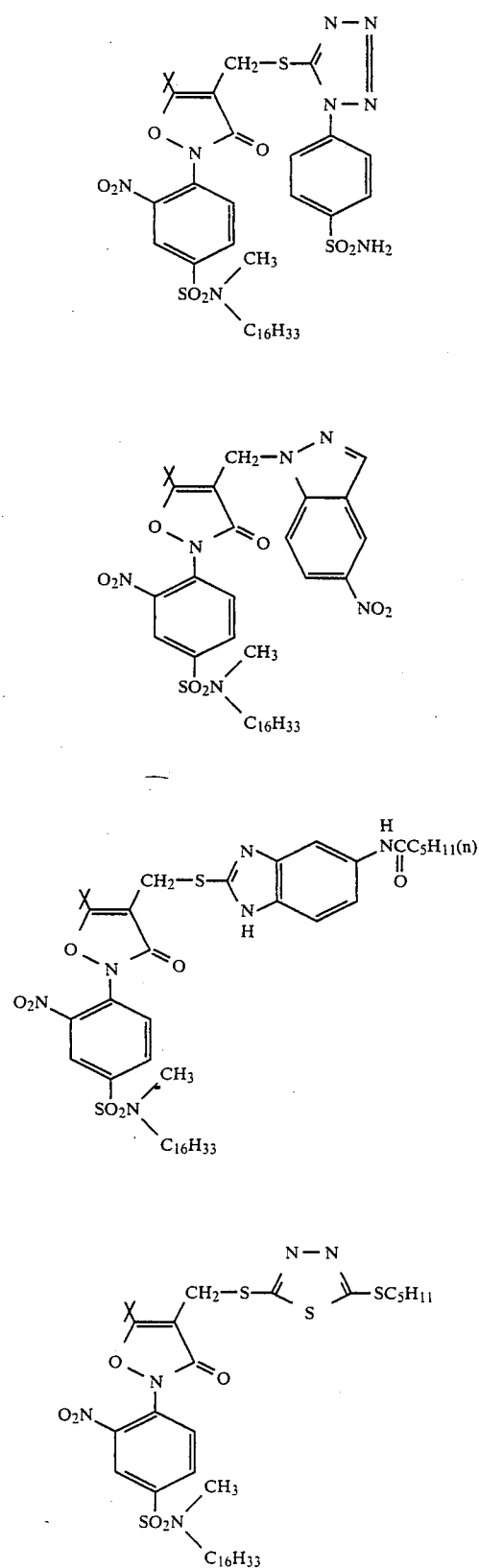

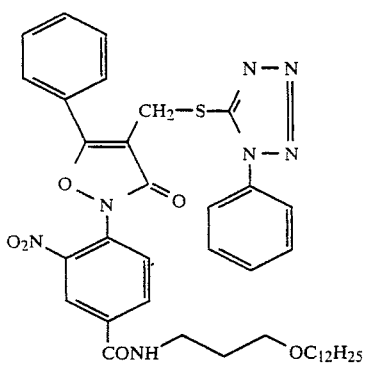
49
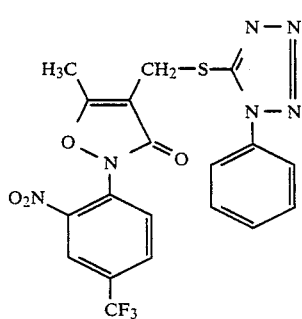
51
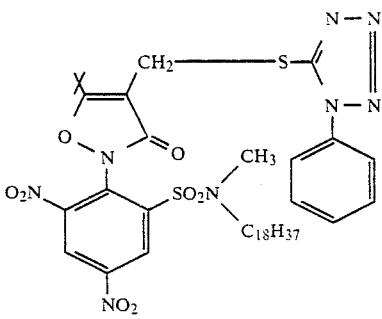
52
or
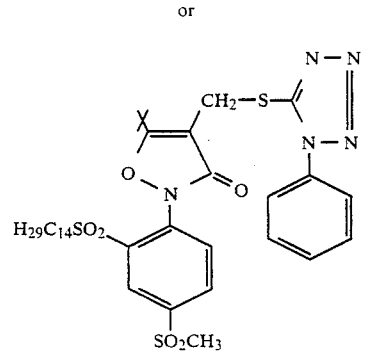
61
* * * * *